United States Patent
Clark et al.

(10) Patent No.: US 6,831,068 B2
(45) Date of Patent: Dec. 14, 2004

(54) MACROLIDE ANTIBACTERIAL COMPOUNDS

(75) Inventors: Richard Clark, Gurnee, IL (US); Stevan Djuric, Libertyville, IL (US); Zhenkun Ma, Dallas, TX (US); Sanyi Wang, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/361,221

(22) Filed: Feb. 10, 2003

(65) Prior Publication Data

US 2004/0009931 A1 Jan. 15, 2004

Related U.S. Application Data

(60) Provisional application No. 60/356,296, filed on Feb. 13, 2002.

(51) Int. Cl.$^7$ .................. A61K 31/70; C07H 17/08
(52) U.S. Cl. .................. 514/29; 536/7.4
(58) Field of Search .................. 514/29; 536/7.4

(56) References Cited

U.S. PATENT DOCUMENTS 6,075,133 A * 6/2000 Or et al. .................. 536/7.2

6,498,146 B1 * 12/2002 Wu .................. 514/29

* cited by examiner

*Primary Examiner*—Elli Peselev
(74) *Attorney, Agent, or Firm*—B. Gregory Donner

(57) ABSTRACT

Antibacterial compounds having formula (I)

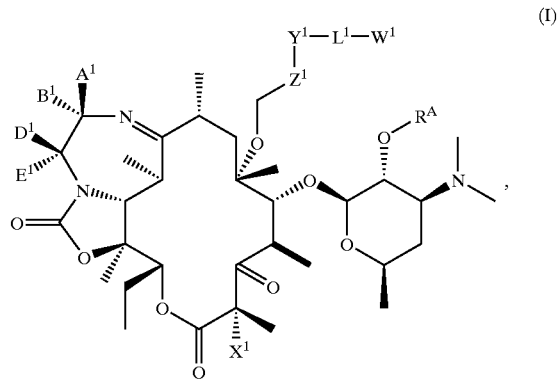

and salts, prodrugs, and salts of prodrugs thereof, processes for making the compounds and intermediates used in the processes, compositions containing the compounds, and methods for prophylaxis or treatment of bacterial infections using the compounds are disclosed.

6 Claims, No Drawings

MACROLIDE ANTIBACTERIAL COMPOUNDS

This application claims priority to commonly-owned U.S. Provisional Patent Application Ser. No. 60/356,296, filed Feb. 13, 2002, the specification of which is hereby incorporated herein by reference.

TECHNICAL FIELD

This invention is directed to compounds with antibacterial activity, processes for making the compounds and intermediates used in the processes, compositions containing the compounds, and methods for prophylaxis or treatment of bacterial infections using the compounds.

BACKGROUND OF THE INVENTION

Because the effectiveness of many drugs currently available for prophylaxis or treatment of bacterial infections is being compromised by the emergence of drug-resistant bacteria, novel antibacterial compounds would be beneficial for their therapeutic value and their contribution to the antibacterial arts.

SUMMARY OF THE INVENTION

A first embodiment of this invention, therefore, is directed to compounds, and salts, prodrugs, and salts of prodrugs thereof, having antibacterial activity, the compounds having formula (I)

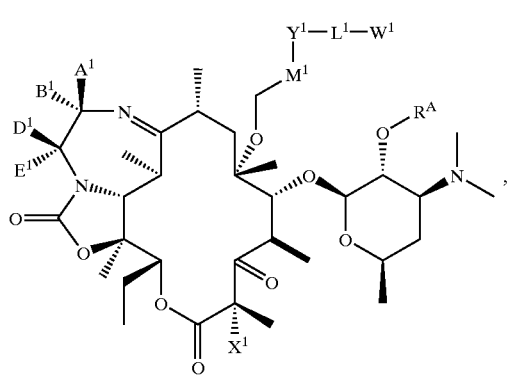

in which two of $A^1$, $B^1$, $D^1$, and $E^1$ are hydrogen, alkyl, alkenyl, alkynyl, cycloalkyl, aryl, heteroaryl, heterocyclyl, —CN, —OH, —SH, —C(O)H, —C(O)$R^1$, —C(O)OH, —C(O)O$R^1$, —C(O)N$R^2R^3$, or alkyl substituted by one, two, or three substituents independently selected from the group consisting of —CN, —OH, —SH, halo, aryl, heteroaryl, heterocyclyl, —O$R^1$, —S$R^1$, —C(O)H, —C(O)$R^1$, —C(O)OH, —C(O)O$R^1$, —CH=N—O$R^1$, —OC(O)$R^1$, —OC(O)O$R^1$, —C(O)N$R^2R^3$, —OC(O)N$R^2R^3$, —N$R^2R^3$, —N($R^4$)C(O)H, —N($R^4$)C(O)$R^1$, —N($R^4$)C(O)N$R^2R^3$, —N($R^4$)SO$_2R^1$, —O$R^1$, —S$R^1$, —S(O)$R^1$, —SO$_2R^1$, and —SO$_2$N$R^2R^3$, and the remainder are hydrogen; or $A^1$ and $D^1$, $A^1$ and $E^1$, $B^1$ and $D^1$, or $B^1$ and $D^1$ together are one- to five-membered alkylene or two to five-membered heteroalkylene, and the remainder are hydrogen; or $A^1$ and $B^1$ together are one- to seven-membered alkylene or two- to seven-membered heteroalkylene, and $D^1$ and $E^1$ are hydrogen; or $D^1$ and $E^1$ together are one- to seven-membered alkylene or two- to seven-membered heteroalkylene, and $A^1$ and $B^1$ are hydrogen;

$X^1$ is hydrogen or fluoride;
$M^1$ is (E)-CH=CH, (Z)-CH=CH, or C≡C;
$Y^1$ is arylene or heteroarylene;
$L^1$ is drawn from left to right and is alkylene, alkenylene, alkynylene, CH=N—O—CH$_2$-(alkenylene), CH$_2$N($R^5$), CH$_2$N($R^5$)(CH$_2$)$_m$, C(O)N($R^5$), N($R^5$)C(O)N($R^6$), CH=N—N($R^5$), CH=N—N($R^5$)C(O), O, CH=N—O, CH=N—O—(CH$_2$)m, C(O)N($R^5$)(CH$_2$)$_m$, or CH=N—O(CH$_2$)$_n$—O, in which m is one, two, three, or four, and n is two, three, or four;

$W^1$ is hydrogen aryl, heteroaryl, or heterocyclyl;
$R^1$ is alkyl, aryl, heteroaryl, or heterocyclyl;
$R^2$ and $R^3$ are independently hydrogen or alkyl; or
$R^2$ and $R^3$ together are 3- to 7-membered alkylene or 3-to 7-membered heteroalkylene;
$R^4$ is hydrogen or alkyl;
$R^5$ and $R^6$ are independently hydrogen or alkyl; and
$R^A$ is hydrogen or $R^P$ in which $R^P$ is a hydroxyl protecting moiety;

in which, for the foregoing, each aryl, arylene, heteroaryl, heteroarylene, heterocyclyl, and heterocycloalkylene is unsubstituted or substituted by one, two, three, four, or five substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —O$R^{30}$, —S$R^{30}$, —S(O)$R^{35}$, —SO$_2R^{35}$, —C(O)H, —C(O)$R^{35}$, —C(O)OH, —C(O)O$R^{35}$, —NH($R^{35}$), —N($R^{35}$)($R^{36}$), —C(O)NH$_2$, —C(O)NH($R^{35}$), —C(O)N($R^{35}$)($R^{36}$), —OC(O)$R^{35}$, —OC(O)O$R^{35}$, —OC(O)NH$_2$, —OC(O)NH($R^{35}$), —OC(O)N($R^{35}$)($R^{36}$), —NHC(O)H, —NHC(O)$R^{35}$, —NHC(O)O$R^{35}$, —NHC(O)NH$_2$, —NHC(O)NH($R^{35}$), —NHC(O)N($R^{35}$)($R^{36}$), —SO$_2$NH$_2$, —SO$_2$NH($R^{35}$), —SO$_2$N($R^{35}$)($R^{36}$), $R^{40}$, and alkyl substituted with one or two substituents independently selected from the group consisting of halo, —CN, —OH, —SH, =O, —O$R^{30}$, —S$R^{30}$, —C(O)OH, —C(O)O$R^{35}$, —NH$_2$, —NH($R^{35}$), —N($R^{35}$)($R^{36}$), —C(O)NH$_2$, —C(O)NH($R^{35}$), —C(O)N($R^{35}$)($R^{36}$), —OC(O)$R^{35}$, —OC(O)NH$_2$, —OC(O)NH($R^{35}$), —OC(O)N($R^{35}$)($R^{36}$), —SO$_2$NH$_2$, —SO$_2$NH($R^{35}$), —SO$_2$N($R^{35}$)($R^{36}$) and $R^{40}$;

$R^{30}$ is alkyl or alkyl substituted with a substituent selected from the group consisting of halo and —O$R^{45}$;

$R^{35}$ and $R^{36}$ are independently selected alkyl;

$R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, tetrazolyl, pyridyl, pyrazinyl, pyrimidinyl, pyrrolidinyl, inidazolidinyl, piperidinyl, piperazinyl, morpholinyl, or thiomorpholinyl, each of which is unsubstituted or substituted with one, two, or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, —O$R^{45}$, —S$R^{45}$, —S(O)$R^{50}$, —SO$_2R^{50}$, —C(O)H, —C(O)$R^{50}$, —C(O)OH, —C(O)O$R^{50}$, —NH$_2$, —NH($R^{50}$), —N($R^{50}$)($R^{51}$), —C(O)NH$_2$, —C(O)NH($R^{50}$), —C(O)N($R^{50}$)($R^{51}$), —OC(O)$R^{50}$, —OC(O)O$R^{50}$, —OC(O)NH$_2$, —OC(O)NH($R^{50}$), —OC(O)N($R^{50}$)($R^{51}$), —NHC(O)H, —NHC(O)$R^{50}$, —NHC(O)O$R^{50}$, —NHC(O)NH$_2$, —NHC(O)NH($R^{50}$), —NHC(O)N($R^{50}$)($R^{51}$), —SO$_2$NH$_2$, SO$_2$NH($R^{50}$), and —SO$_2$N($R^{50}$)($R^{51}$);

$R^{45}$ is alkyl; and
$R^{50}$ and $R^{51}$ are independently selected alkyl.

A second embodiment of this invention is directed to processes for making the compounds of the first embodiment.

A third embodiment of this invention is directed to intermediates which are useful in the second embodiment.

A fourth embodiment of this invention is directed to compositions comprising a therapeutically effective amount of a compound of the first embodiment.

A fifth embodiment of this invention is directed to methods for prophylaxis or treatment of bacterial infections in a fish or a mammal comprising administering thereto a therapeutically effective amount of a compound of the first embodiment.

In a preferred fifth embodiment of this invention, the beneficiary of prophylaxis or treatment of bacterial infections is a mammal.

In a more preferred fifth embodiment of this invention, the beneficiary of prophylaxis or treatment of bacterial infections is a human.

DETAILED DESCRIPTION OF THE INVENTION

The compounds of this invention comprise both fixed and variable moieties, the latter of which are identified by a capital letter and accompanying numerical or alphabetical superscript, in which the term "alkenyl" means a monovalent, straight or branched hydrocarbon, having two to eight carbon atoms and at least one carbon-carbon double bond, attached through a carbon atom;

the term "alkenylene" means a divalent, straight or branched hydrocarbon, having two to eight carbon atoms and one carbon-carbon double bond, attached through carbon atoms;

the term "alkynyl" means a monovalent, straight or branched hydrocarbon, having two to eight carbon atoms and at least one carbon-carbon triple bond, attached through a carbon atom;

the term "alkynylene" means a divalent, straight or branched hydrocarbon, having two to eight carbon atoms and one carbon-carbon triple bond, attached through carbon atoms;

the term "alkyl" means a monovalent, saturated, straight or branched hydrocarbon, having one to eight carbon atoms, attached through a carbon atom;

the term "alkylene" means a divalent, saturated, straight or branched hydrocarbon, having one to eight carbon atoms, attached through carbon atoms;

the term "aryl" means monovalent phenyl, attached through a carbon atom, unfused or fused with cycloalkyl, cycloalkenyl, heteroaryl, another phenyl, naphthyl, or the saturated part of indan;

the term "arylene" means divalent phenyl, attached through phenyl carbon atoms, unfused or fused with cycloalkyl, cycloalkenyl, another phenyl, naphthyl, or the saturated part of indan;

the term "cycloalkenyl" means a monovalent, cyclic or bicyclic hydrocarbon, having four to eight carbon atoms and one or two carbon-carbon double bonds, attached through a carbon atom;

the term "cycloalkyl" means a monovalent, saturated cyclic hydrocarbon, having three to eight carbon atoms, attached through a carbon atom;

the term "cycloalkylene" means a divalent, saturated cyclic hydrocarbon, having three to eight carbon atoms, attached through carbon atoms;

the term "halo" means fluoro (—F), chloro (—Cl), bromo (—Br), and iodo (—I);

the term "heteroaryl" means a monovalent, aromatic, five-membered ring having two double bonds and one oxygen or one sulfur atom, one, two, three, or four nitrogen atoms, or one or two nitrogen atoms and one oxygen or one sulfur atom and the remaining atoms are carbon atoms, attached through a carbon or nitrogen atom, and unfused or fused with phenyl, cycloalkyl, cycloalkenyl, heterocycle, or another heteroaryl; and a monovalent aromatic, six-membered ring having three double bonds and one, two, or three nitrogen atoms and the remaining atoms are carbon atoms, attached through a carbon atom and unfused or fused with phenyl, cycloalkyl, cycloalkenyl, heterocycle, or another heteroaryl;

the term "heteroarylene" means a divalent, aromatic, five-membered ring having two double bonds and one oxygen or one sulfur atom, one, two, three, or four nitrogen atoms, or one or two nitrogen atoms and one oxygen or one sulfur atom and the remaining atoms are carbon atoms, attached through carbon atoms; and a divalent aromatic, six-membered ring having three double bonds and one, two, or three nitrogen atoms and the remaining atoms are carbon atoms, attached through carbon atoms;

the term "heterocyclyl" means a monovalent, non-aromatic three- or four-membered ring having one nitrogen, oxygen, or sulfur atom and the remaining atoms are carbon atoms, zero double bonds, attached through a carbon or nitrogen atom and unfused or fused with phenyl or heteroaryl; a monovalent, non-aromatic five-membered ring having one or two nitrogen, oxygen, or sulfur atoms, and the remaining atoms are carbon atoms, and zero or one double bonds, attached through a carbon or nitrogen atom and unfused or fused with phenyl or heteroaryl; and a monovalent, non-aromatic six or seven-membered ring having one, two, or three nitrogen, oxygen, or sulfur atoms and the remaining atoms are carbon atoms, and zero, one, or two double bonds, attached through a carbon or nitrogen atom and unfused or fused with phenyl or heteroaryl; and the term "heteroalkylene" means an alkylene of three to eight atoms, connected through a carbon atom, in which one, two, or three $CH_2$ moieties have been independently replaced by O, NH, N(alkyl), S, C(O), S(O), or $SO_2$.

Preferred $A^1$, $B^1$, $D^1$, and $E^1$ moieties are hydrogen.

A preferred $X^1$ moiety is hydrogen.

A preferred $M^1$ moiety is C≡C.

Preferred $Y^1$ moieties are 1,3-phenylene, 1,4-phenylene, and 2,5-thienylene.

Preferred $L^1$ moieties are alkynylene, CH=N—O—$CH_2$-(alkenylene), $CH_2$N($R^5$), $CH_2$N($R^5$)$(CH_2)_m$, C(O)N($R^5$), N($R^5$)C(O)N($R^6$), CH=N—N($R^5$), CH=N—N($R^5$)C(O), O, CH=N—O, CH=N—O$(CH_2)$m, C(O)N($R^5$)$(CH_2)_m$, and CH=N—O$(CH_2)_n$—O, in which m is one to three, and n is three.

Preferred $W^1$ moieties are phenyl, 3-fluorophenyl, 4-(1,2,3-thiadiazol-4-yl)phenyl, phenyl fused with another phenyl (naphthyl), pyridyl, and pyridyl fused with phenyl (quinolinyl).

Preferred $R^5$ moieties are hydrogen and alkyl.

A preferred $R^6$ moiety is hydrogen.

A preferred $R^A$ moiety is hydrogen.

These preferred variable moieties combine with the parent moiety to form a preferred first embodiment of this invention, the preferred first embodiment comprising compounds, and salts, prodrugs, and salts of prodrugs thereof, having formula (I)

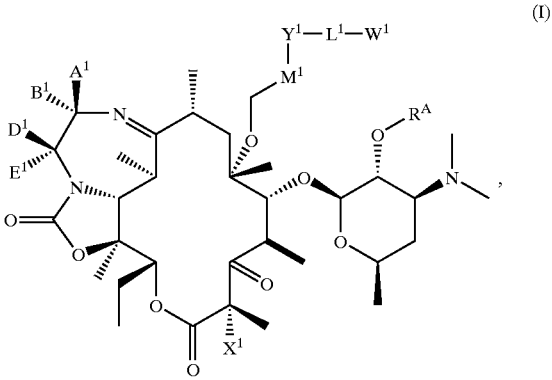

(I)

in which $A^1$, $B^1$, $D^1$, and $E^1$ are hydrogen; $X^1$ is hydrogen; $M^1$ is C≡C; $Y^1$ is arylene or heteroarylene, in which the $Y^1$ arylene is 1,3-phenylene or 1,4-phenylene, and in which the $Y^1$ heteroarylene is 2,5-thienylene; $L^1$ is drawn from left to right and is alkynylene, CH=N—O—CH$_2$-(alkenylene), CH$_2$N(R$^5$), CH$_2$N(R$^5$)(CH$_2$)$_m$, C(O)N(R$^5$), N(R$^5$)C(O)N(R$^6$), CH=N—N(R$^5$), CH=N—N(R$^5$)C(O), O, CH=N—O, CH=N—O(CH$_2$)$_m$, C(O)N(R$^5$)(CH$_2$)$_m$, or CH=N—O(CH$_2$)$_n$—O, in which m is one, two, or three, and n is three; $W^1$ is hydrogen, aryl, or heteroaryl, in which the aryl is phenyl or phenyl fused with another phenyl (naphthyl), each of which is unsubstituted or substituted by one substituent selected from the group consisting of halo and $R^{40}$, in which $R^{40}$ is 1,2,3-thiadiazolyl, and in which the heteroaryl is pyridyl or pyridyl fused with phenyl (quinolinyl); with the proviso that $W^1$ is hydrogen only when $L^1$ is CH=N—O(CH$_2$)$_m$; $R^5$ is hydrogen or alkyl; $R^6$ is hydrogen; and $R^A$ is hydrogen.

These preferred variable moieties also combine to form another preferred first embodiment of this invention, the preferred first embodiment comprising compounds, and salts, prodrugs, and salts of prodrugs thereof, having formula (I)

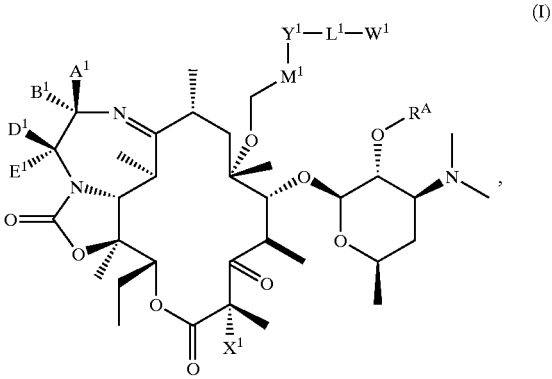

(I)

in which $A^1$, $B^1$, $D^1$, and $E^1$ are hydrogen; $X^1$ is hydrogen; $M^1$ is C≡C; $Y^1$ is arylene or heteroarylene, in which the arylene is 1,3-phenylene or 1,4-phenylene, and in which the heteroarylene is 2,5-thienylene; $L^1$ is drawn from left to right and is C$_2$-alkynylene, CH=N—O—CH$_2$—(C$_2$-alkenylene), CH$_2$N(R$^5$), CH$_2$N(R$^5$)(CH$_2$)$_m$, C(O)N(R$^5$), N(R$^5$)C(O)N(R$^6$), CH=N—N(R$^5$), CH=N—N(R$^5$)C(O), O, CH=N—O, CH=N—O(CH$_2$)$_m$, C(O)N(R$^5$)(CH$_2$)$_m$, or CH=N—O(CH$_2$)$_n$—O, in which m is one, two, or three, and n is three; $W^1$ is hydrogen, aryl, heteroaryl, or heterocyclyl, in which the aryl is phenyl or phenyl fused with another phenyl (naphthyl), each of which is unsubstituted or substituted by one substituent selected from the group consisting of halo and $R^{40}$, in which $R^{40}$ is 1,2,3-thiadiazolyl, and in which the heteroaryl is pyridyl or pyridyl fused with phenyl (quinolinyl); with the proviso that $W^1$ is hydrogen only when $L^1$ is CH=N—O(CH$_2$)$_m$ and m is one; $R^5$ is hydrogen or C$_1$-alkyl; $R^6$ is hydrogen; and $R^A$ is hydrogen.

These preferred variable moieties also combine to form still yet another preferred first embodiment of this invention, the preferred first embodiment comprising compounds, and salts, prodrugs, and salts of prodrugs thereof, which are (2R,4R,5R,6R,8R,11R,12S,19R,20R)-11-ethyl-2,4,6,8,12,19-hexamethyl-7,9,14-trioxo-4-(3-(5-((phenylamino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-(((phenylmethyl)oxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-((methyloxy)imino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-((phenyloxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-(((naphthalen-1-ylmethyl)oxy)imino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-(((3-naphthalen-1-ylprop-2-enyl)oxy)imino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-(((2-(phenyloxy)ethyl)oxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-(((phenylmethyl)amino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-(pyridin-2-ylhydrazono)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, N'-((1E)-(5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)thien-2-yl)methylidene)pyridine-2-carbohydrazide, (2R,4R,5R,6R,8R,11R,12S,19R,20R)-11-ethyl-2,4,6,8,12,19-hexamethyl-7,9,14-trioxo-4-(3-(5-((E)-(((quinolin-3-ylmethyl)oxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-(((2-phenylethyl)amino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-(((3-phenylpropyl)amino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(3-(pyridin-2-yloxy)phenyl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, 5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)-N-(3-fluorophenyl)thiophene-2-carboxamide, 5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)-N-(3-fluorophenyl)-N-methylthiophene-2-carboxamide, (2R,4R,5R,6R,8R,11R,12S,19R,20R)-11-ethyl-4-(3-(3-((3-fluorophenyl)oxy)phenyl)prop-2-ynyl)-2,4,6,8,12,19-hexamethyl-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-(pyridin-2-ylethynyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(4-(phenyloxy)phenyl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, 5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)-N-pyridin-3-ylthiophene-2-carboxamide, 5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)-N-(4-(1,2,3-thiadiazol-4-yl)phenyl)thiophene-2-carboxamide, 5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)-N-(3-quinolin-3-ylpropyl)thiophene-2-carboxamide, (2R,4R,5R,6R,8R,11R,12S,19R,20R)-11-ethyl-2,4,6,8,12,19-hexamethyl-4-(3-(5-((methyl(phenylmethyl)amino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, and N-(5-(3-((2R,4R,5R,6R,8R,11R,12S,19R,20R)-11-ethyl-2,4,6,8,12,19-hexamethyl-7,9,14-trioxo-5-((3,4,6-trideoxy-3-(dimethylamino)-β-D-xylo-hexopyranosyl)oxy)-10,13-dioxa-15,18-diazatricyclo[10.6.2.0$^{15,20}$]icos-1(18)-en-4-yl)prop-1-ynyl)thien-2-yl)-N'-pyridin-4-ylurea.

The compounds of this invention comprise asymmetrically substituted carbon atoms in the R or S configuration. Asymmetric carbon atoms with equimolar amounts of R and S configurations are racemic. Atoms with an excess of one configuration over the other are assigned the configuration in the higher amount, preferably an excess of about 85%–90%, more preferably an excess of about 95%–99%, and still more preferably an excess greater than about 99%.

The terms "R" and "S" are as defined by the IUPAC 1974 Recommendations for Section E, Fundamental Stereochemistry, Pure Appl. Chem. (1976) 45, 13–10.

Accordingly, all stereoisomers of the compounds of this invention, including racemic mixtures, mixtures of diastereomers, and single diastereomers, are meant to be embraced by this invention.

The compounds of this invention may also comprise carbon-carbon double bonds as being in the Z or E configuration, in which the term "Z" represents the larger two of the four substituents disposed on same side of a carbon-carbon double bond and the term "E" represents the larger two of the four substituents disposed on opposite sides of a carbon-carbon double bond. The compounds may also exist as an equilibrium mixture comprising Z or E configurations.

The compounds of this invention containing hydroxyl, amino, or carboxylic acids may have attached thereto prodrug-forming moieties. The prodrug-forming moieties are removed by metabolic processes and release the compounds having the freed hydroxyl, amino, or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

The compounds of this invention may be prepared by synthetic processes or metabolic processes. Metabolic processes include those processes occurring in vitro in vivo.

The compounds of this invention may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, formate, fumarate, hydrochloride, hydrobromide, hydroiodide, lactate, maleate, mesitylenesulfonate, methanesulfonate, naphthylenesulfonate, nicotinate, oxalate, pamoate, pectinate, persulfate, picrate, propionate, succinate, tartrate, thiocyanate, trichloroacetic, trifluoroacetic, phosphate, glutamate, bicarbonate, paratoluenesulfonate, lactobionate, and undecanoate salts of the compounds and prodrugs thereof are contemplated as being within the scope of this invention. When the compounds contain carboxylic acids, basic addition salts may be prepared therefrom by reaction with a base such as the hydroxide, carbonate, or bicarbonate-of cations such as lithium, sodium, potassium, calcium, and magnesium.

The compounds of this invention may be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, cocoa butter, gelatin, isotonic saline, malt, powdered tragacanth, Ringer's solution, talc, water, aluminum hydroxide, magnesium hydroxide, sodium and potassium phosphate salts, cellulose, cellulose acetate, ethyl cellulose, sodium carboxymethyl cellulose, ethyl laureate, ethyl oleate, magnesium stearate, sodium lauryl sulfate, castor oil, corn oil, cottonseed oil, germ oil, groundnut oil, olive oil, peanut oil, safflower oil, sesame oil, soybean oil, benzyl alcohol, benzyl benzoate, 1,3-butylene glycol, ethanol, ethyl acetate, ethyl carbonate, glycerol, isopropanol, propylene glycol, tetrahydrofurfuryl alcohol, corn starch, potato starch, lactose, glucose sucrose, and mixtures thereof. Excipients for ophthalmically and orally administered compounds in liquid dosage forms include water, ethanol, isopropanol, ethyl carbonate, ethyl acetate, benzyl alcohol, benzyl benzoate, propylene glycol, 1,3-butylene glycol, cottonseed oil, groundnut oil, corn oil, germ oil, olive oil, castor oil, sesame oil, glycerol, tetrahydrofurfuryl alcohol, polyethylene glycols, fatty acid esters of sorbitan, and mixtures thereof. Excipients for osmotically administered compounds include water, ethanol, isopropanol, chlorofluorohydrocarbons, and mixtures thereof. Excipients for parenterally administered compounds include water, 1,3-butanediol, Ringer's solution, U.S.P. or isotonic sodium chloride solution, oleic acid, castor oil, corn oil, cottonseed oil, germ oil, groundnut oil, olive oil, peanut oil, safflower oil, sesame oil, soybean oil, liposomes, and mixtures thereof. Excipients for rectally and vaginally administered compounds include cocoa butter, polyethylene glycol, wax, and mixtures thereof.

The compounds of this invention may be administered parenterally (subcutaneously, intravenously, intramuscularly, and intrasternally), orally, osmotically, ophthalmically, rectally, topically, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups. Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous suspensions, the latter of which contains crystalline, amorphous, or otherwise insoluble forms of the compounds. Rectally and vaginally administered compounds may be administered as creams, gels, lotions, ointments, and pastes.

Dosage forms for the compounds of this invention depend on the species being treated, the disorder being treated and the severity thereof, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

To determine antibacterial activity of the compounds of this invention, twelve petri dishes, each containing successive aqueous dilutions of test compounds in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing Streptococcus strains), co-incubated at 35–37° C. for 20–24 hours with a plate with an erythromycin A standard and a control plate with no compound, and inspected visually to provide the minimum inhibitory concentration (MIC), in $\mu$g/mL, by which is meant the lowest concentration of the test compound which yielded no growth, a slight haze, or sparsely isolated colonies on the inoculum spot as compared to growth in the control plate.

TABLE 1

| Microorganism | Code |
| --- | --- |
| *Staphylococcus aureus* NCTC10649M | AA |
| *Staphylococcus aureus* A5177 | BB |
| *Staphylococcus aureus* PIU 2043 | CC |
| *Streptococcus pyogenes* EES61 | DD |
| *Streptococcus pyogenes* 930 | EE |
| *Streptococcus pyogenes* PIU 2548 | FF |
| *Streptococcus pneumoniae* ATCC 6303 | GG |
| *Streptococcus pneumoniae* 5979 | HH |
| *Streptococcus pneumoniae* 5649 | JJ |

All of the compounds of this invention tested displayed antibacterial activity superior to their respective controls and are therefore useful as antibacterials.

The following schemes illustrate representative processes by which the compounds of this invention may be prepared, with the understanding that the order of the steps in the processes may be varied, other reagents may be substituted for those specifically mentioned, and vulnerable substituents may be protected and deprotected during the process.

Abbreviations used are: DME for 1,2-dimethoxyethane; DMF for N,N-dimethylformamide; and THF for tetrahydrofuran.

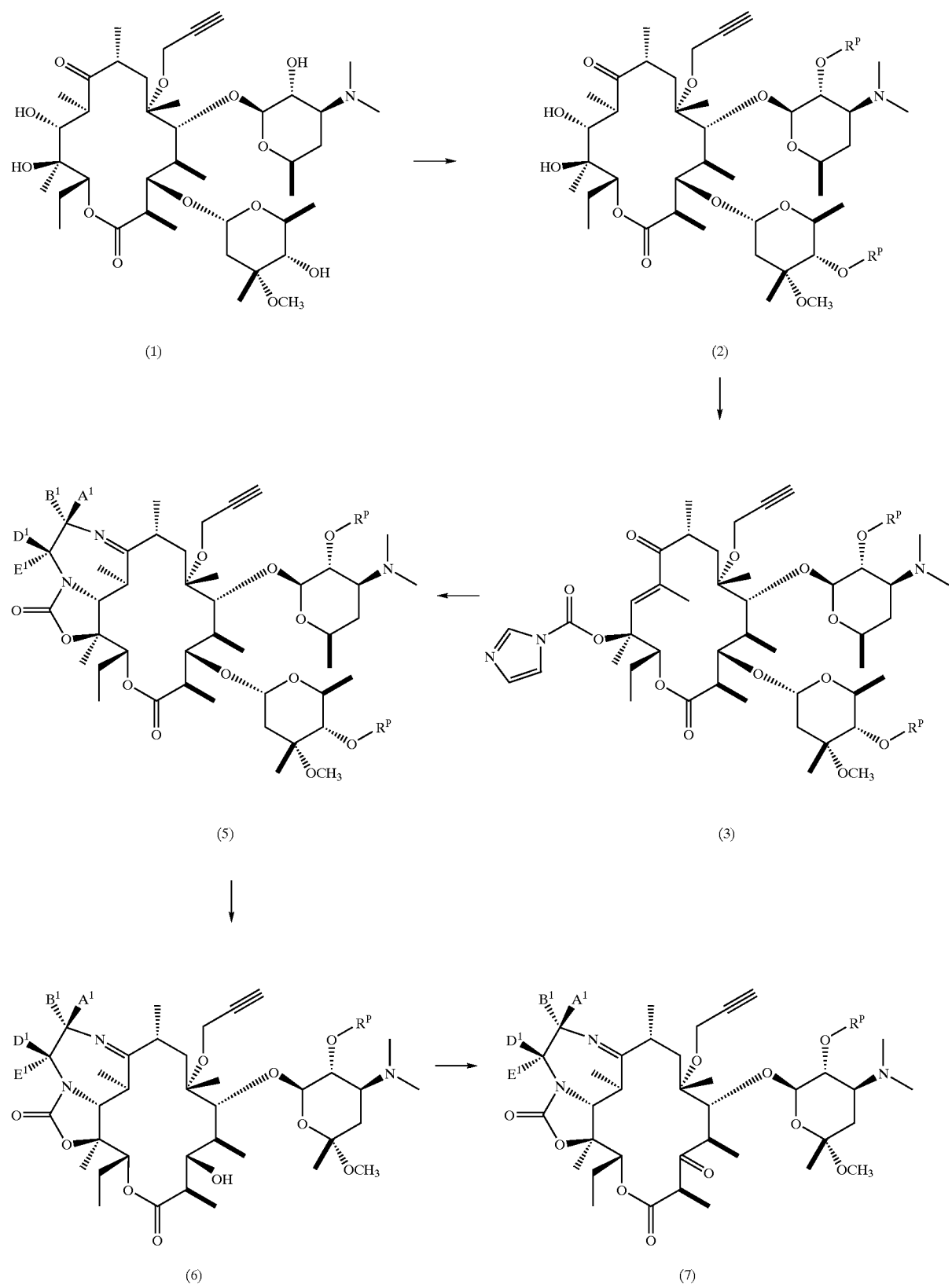

Compounds having formula (1) may be converted to compounds having formula (2), in which $R^P$ is acetyl ($CH_3C(O)$), benzoyl ($C_6H_5C(O)$), or trimethylsilyl, by reacting the former, a hydroxyl protecting reagent, a first base, and, optionally, N,N-dimethylaminopyridine. Hydroxyl protecting reagents include benzoic anhydride, acetic anhydride, benzoyl chloride, acetyl chloride, and trimethylsilyl chloride. First bases include triethylamine, diisopropylethylamine, pyridine, and lutidine. The reaction is typically conducted at about 0° C. to 60° C., over about 4 to 24 hours, in solvents such as dichloromethane, chloroform, THF, DME, and tert-butyl methylether.

Compounds having formula (2) may be converted to compounds having formula (3) by reacting the former, carbonyldiimidazole, a second base, and, optionally, N,N-dimethylaminopyridine. Second bases include 1,8-diazabicyclo-[5.4.0]undec-7-ene, lithium bis(trimethylsilyl)amide, sodium bis(trimethylsilyl)amide, and potassium bis(trimethylsilyl)amide. The reaction is typically conducted at about 25° C., over about 6 to 24 hours, in solvents such as THF, DMF, 1,4-dioxane, and N-methylpyrrolidine.

Compounds having formula (3) may be converted to compounds having formula (5) by (a) reacting the former and a compound having formula (4)

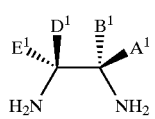

(4)

and (b) reacting the product of step (a) with a dilute first acid. First acids include hydrochloric acid, triflic acid, para-toluenesulfonic acid, and trifluoroacetic acid. Step (a) is typically conducted at about 25° C., over about 24 hours to 72 hours, in solvents such as acetonitrile, DMF, water, and mixtures thereof. Step (b) is typically conducted at about 70° C. to 100° C., over about 12 hours to about 24 hours, in solvents such as benzene, toluene, xylene, and mixtures thereof.

Compounds having formula (5) may be converted to compounds having formula (6) by reacting the former and a second acid. Second acids include hydrochloric acid, triflic acid, para-toluenesulfonic acid, and trifluoroacetic acid. The reaction is typically conducted at about 60° C., over about 12 to 24 hours, in solvents such as ethanol, acetone, THF, water, and mixtures thereof.

Compounds having formula (6) may be converted to compounds having formula (7) by reacting the former, a first oxidizing agent, and, optionally, a first additive. First oxidizing agents include dimethylsulfide/N-chlorosuccinimide, dimethylsulfoxide/1-(3-dimethylaminopropyl)-3-ethylcarbodiimide, and dimethylsulfoxide/oxalyl chloride. First additives include phosphoric acid, pyridinium trifluoroacetate, silica gel, triethylamine, and pyridine. The reaction is typically conducted at about −10° C. to 25° C., over about 3 to 24 hours, in solvents such as THF, DMSO, and dichloromethane.

SCHEME 2

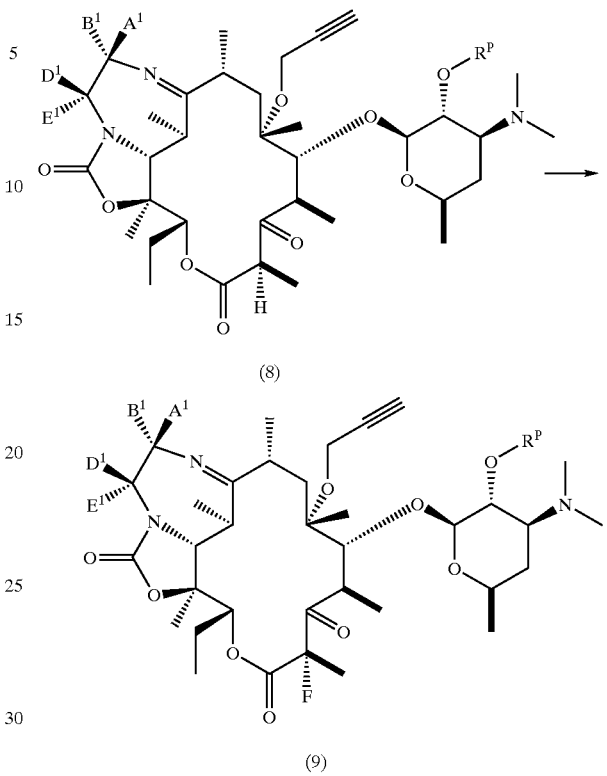

Compounds having formula (8) may be converted to compounds having formula (9) by reacting the former, a fluorinating agent, and, optionally, a third base. Fluorinating agents include 3,5-dichloro-1-fluoropyridinium tetrafluoroborate, N-fluorobenzenesulfonimide, 3,5-dichloro-1-fluoropyridinium triflate, N-fluoro-N-methyl-para-toluenesulfonamide, N-fluoropyridinium triflate, or N-fluoroperfluoropiperidine. Third bases include sodium hydride, potassium hydride, lithium diisopropylamide, triethylamine, and N,N-diisopropylethylamine. The reactions are typically conducted at about −78° C. to 0° C., over about 2 to 24 hours, in solvents such as DMF, THF, and diethyl ether.

SCHEME 3

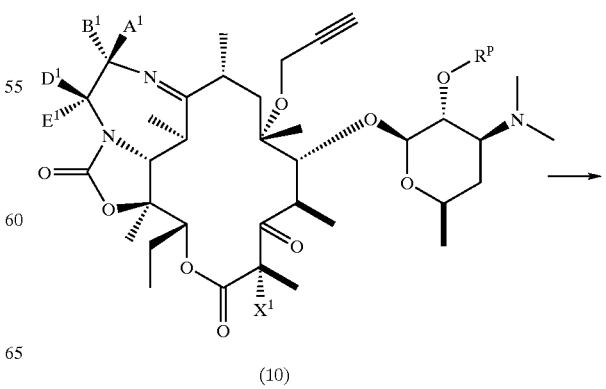

-continued

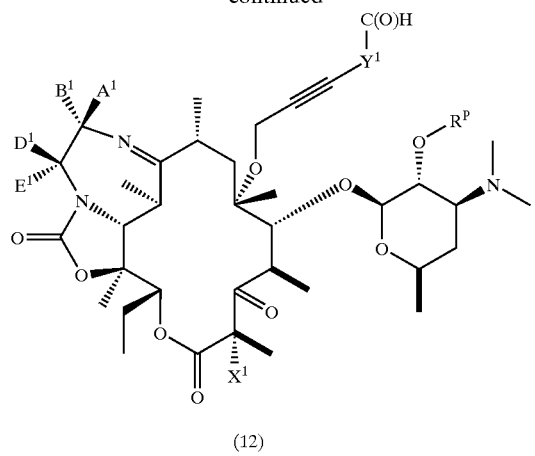

(12)

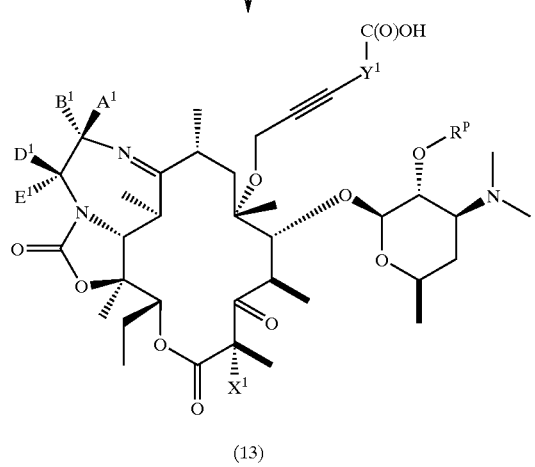

(13)

Compounds having formula (10) may be converted to compounds having formula (12) by reacting the former, a compound having formula (11)

$$Q^1-Y^1-C(O)H \qquad (11),$$

in which $Q^1$ is Cl, Br, or I,
a first base, a coupling catalyst, and, optionally, a second additive. Coupling catalysts include dichlorobis(triphenylphosphine)palladium(II), tris(dibenzylideneacetone)dipalladium(0), tetrakis(triphenylphosphine)palladium(0), and dichlorobis(triphenylphosphine)nickel(II). Second additives include triphenylphosphine, triphenylarsine, 1,2-bis(diphenylphosphino)butane, 1,2-bis(diphenylphosphino)ethane, copper(I) iodide, and mixtures thereof. The reactions are typically conducted at about 50° C. to 80° C., over about 12 to 48 hours, in solvents such as acetonitrile, DME, THF, and mixtures thereof.

Compounds having formula (12) may be converted to compounds having formula (13) by reacting the former and a second oxidizing agent. Second oxidizing agents include molecular oxygen, potassium permanganate, sodium chlorite, and silver oxide. The reactions are typically conducted at about 0° C. to 35° C., over about 1 to 48 hours, in solvents such as acetonitrile, DME, THF, tert-butanol, water, and mixtures thereof.

SCHEME 4

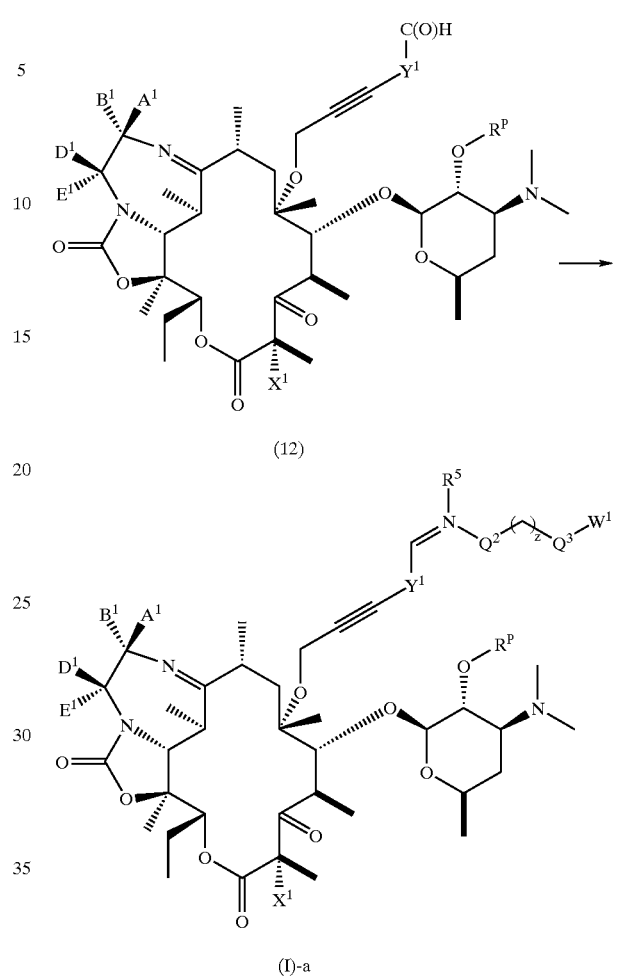

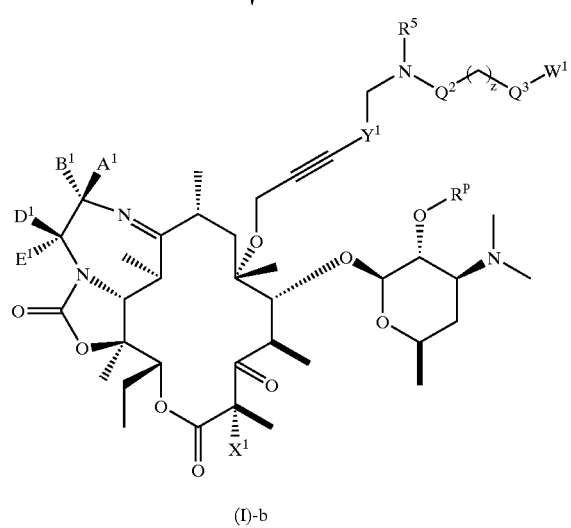

Compounds having formula (12) may be converted to compounds having formula (I)-a by reacting the former and a compound having formula (14)

HN(R⁵)-Q²-(CH₂)$_z$-Q³-W¹     (14)

in which Q² is absent, O, or N(R⁵);

z is zero to four;

Q³ is absent, O, or alkenylene; and in which Q², z, and Q³ may combine with the fixed moieties between Y¹ and W¹ to form moieties represented by L¹, and the dilute first acid. The reaction is typically conducted at about 25° C., over about 24 hours to 72 hours, in solvents such as acetonitrile, DMF, water, and mixtures thereof.

Compounds having formula (I)-a may be converted to compounds having formula (I)-b by reacting the former and a reducing agent. Reducing agents include sodium cyanoborohydride and sodium borohydride. The reaction is typically conducted at about 0° C. to 25° C., over about 24 hours to 72 hours, in solvents such as methanol, ethanol, iso-propyl alcohol, acetonitrile, DMF, water, and mixtures thereof.

Compounds having formula (13) may be converted to compounds having formula (I)-c by reacting the former, a compound having formula (15)

HN(R⁵)(CH₂)$_z$-Q³-W¹     (15), and a dehydrating agent. Dehydrating agents include 1,3-dicyclohexylcarbodiimide and 1-(3-dimethylaminopropyl)-3-ethylcarbodiimide. The reaction is typically conducted at about 0° C. to 25° C., over about 24 hours to 72 hours, in solvents such as acetonitrile, DMF, water, and dichloromethane.

Compounds having formula (13) may be converted to compounds having formula (I)-d by (a) reacting the former and diphenylphosphoryl azide to form a compound having formula (16) and (b) reacting the product of step (a) with a compound having formula (17)

HN(R⁶)(W¹)     (17).

Step (a) is typically conducted at about 25° C. to 80° C., over about 1 to 8 hours, in solvents such as benzene, toluene,

SCHEME 5

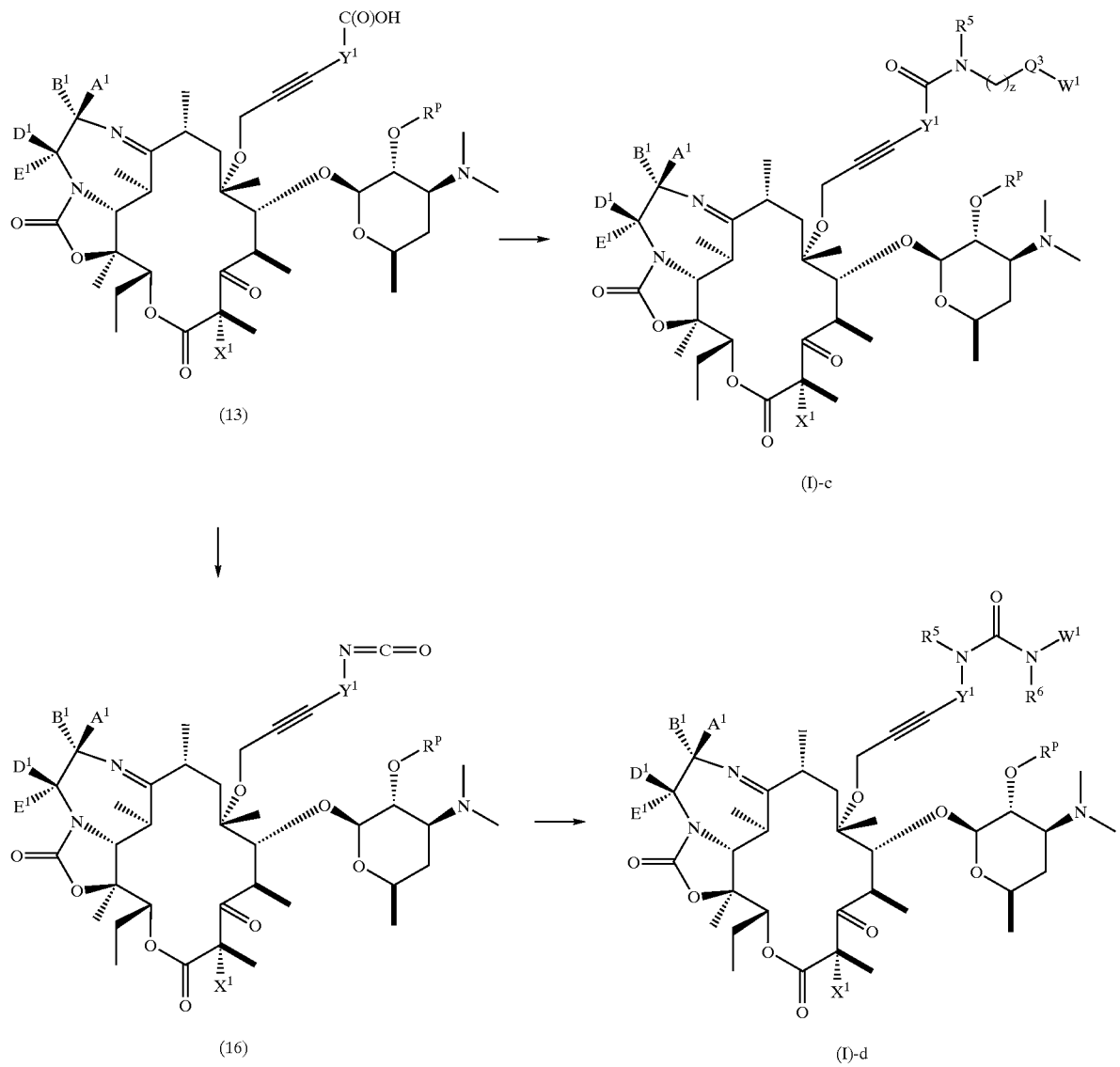

and acetonitrile. Step (b) is typically conducted at about 25° C. to 100° C., over about 1 to 24 hours, in solvents such as benzene, toluene, and acetonitrile, DMF, and DME.

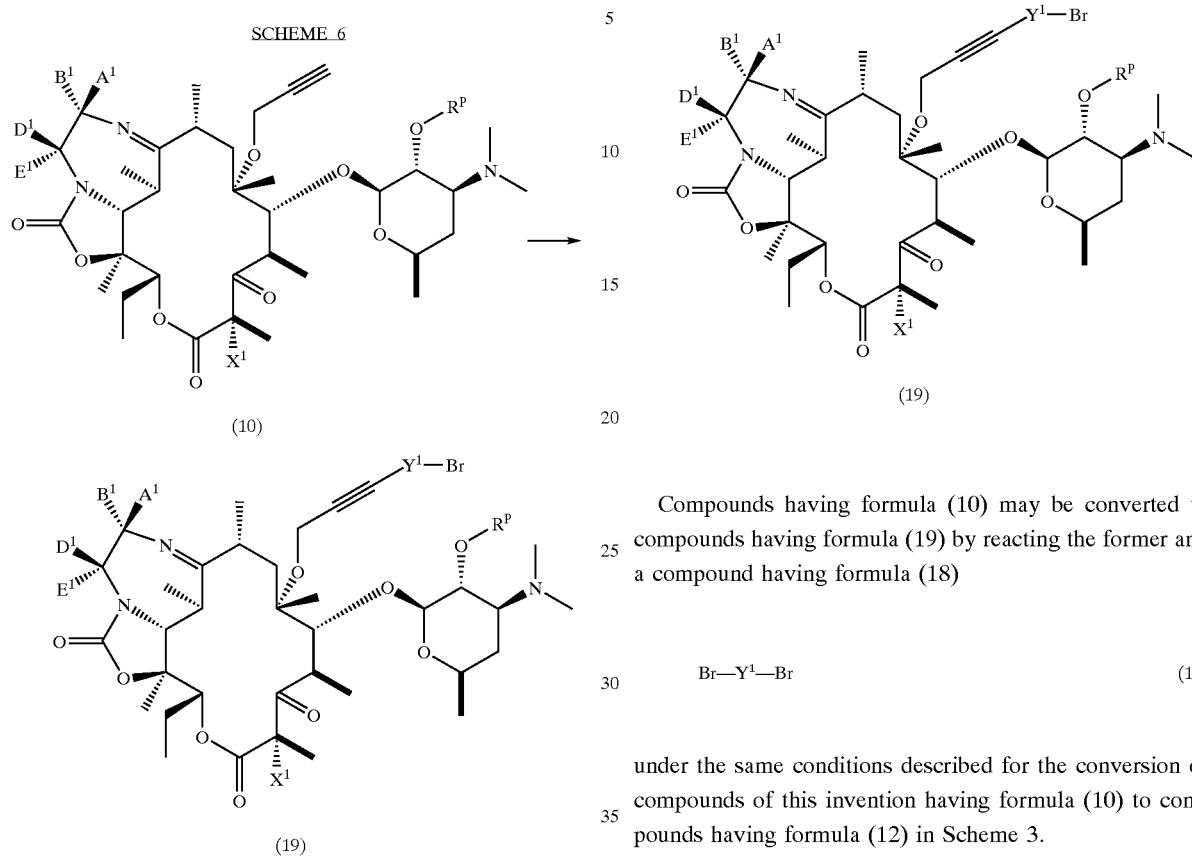

Compounds having formula (10) may be converted to compounds having formula (19) by reacting the former and a compound having formula (18)

$$Br-Y^1-Br \qquad (18)$$

under the same conditions described for the conversion of compounds of this invention having formula (10) to compounds having formula (12) in Scheme 3.

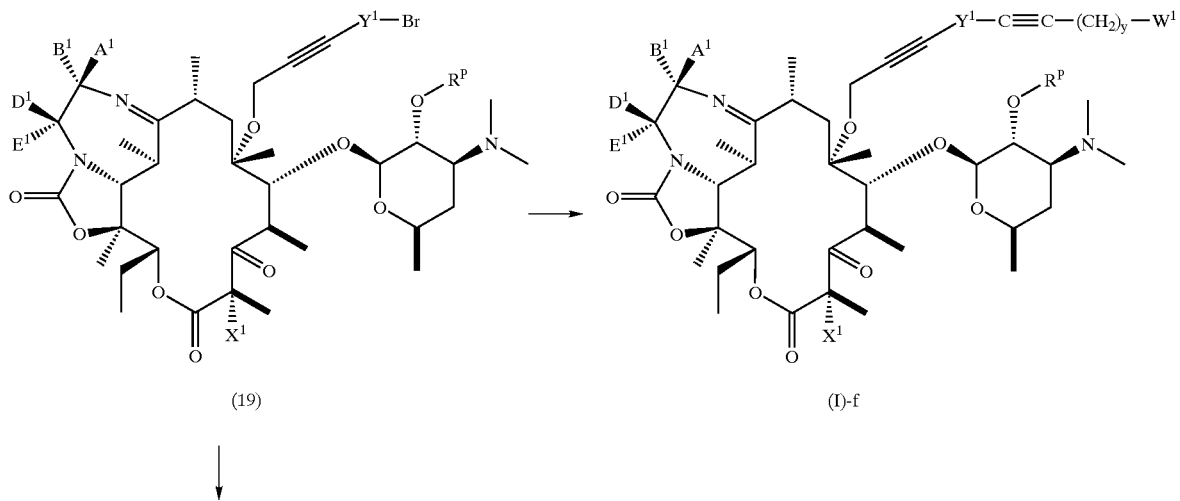

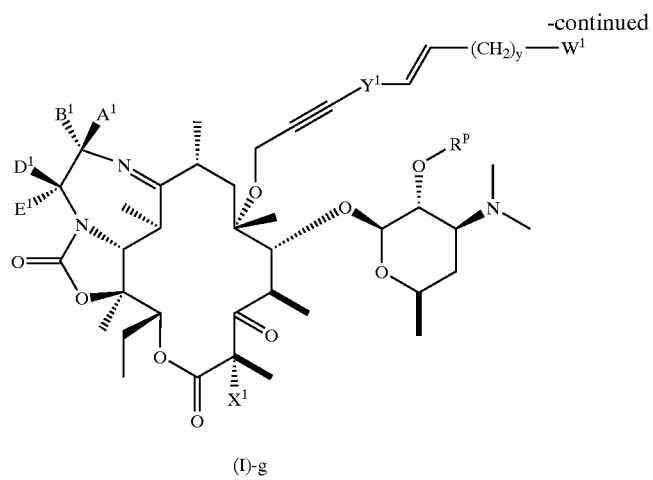

(I)-g

Compounds having formula (19) may be converted to compounds having formula (I)-f by reacting the former and a compound having formula (20)

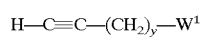

in which y is zero to four, or compounds having formula (I)-g by reacting the former and a compound having formula (21)

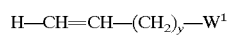

under the same conditions described for the conversion of compounds having formula (10) to compounds having formula (12) in Scheme 3.

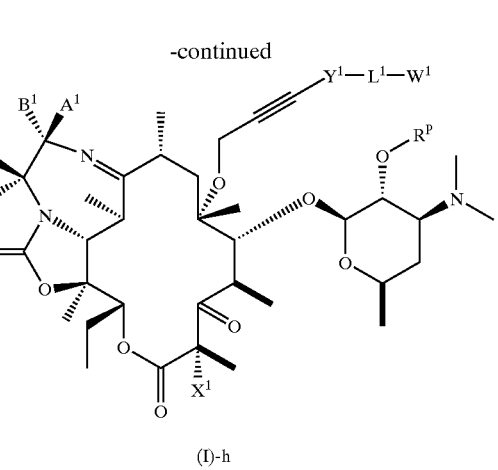

(I)-h

Compounds having formula (10) may be converted to compounds having formula (I)-h by reacting the former and a compound having formula (22)

$$Q^1\text{-}Y^1\text{-}L^1\text{-}W^1 \quad (22)$$

under the same conditions described for the conversion of compounds having formula (10) to compounds having formula (12) in Scheme 3.

SCHEME 8

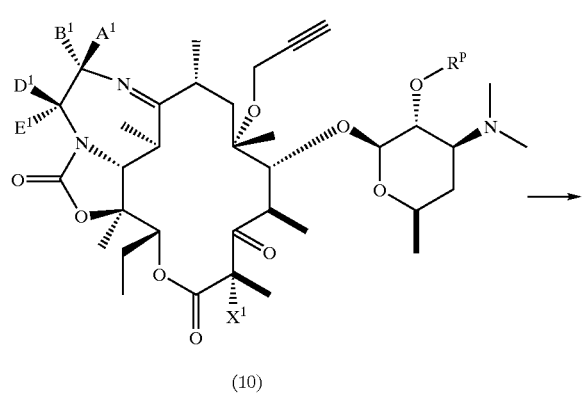

(10)

SCHEME 9

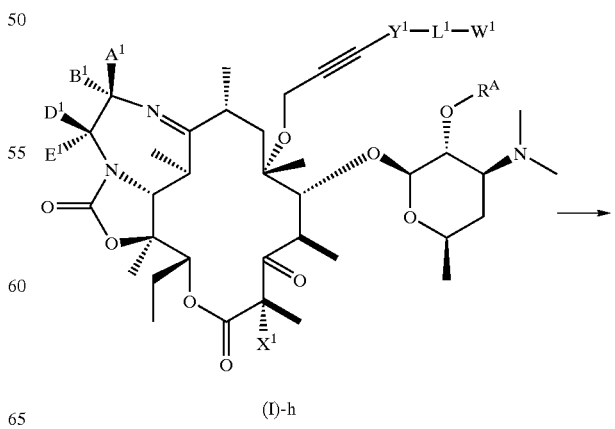

(I)-h

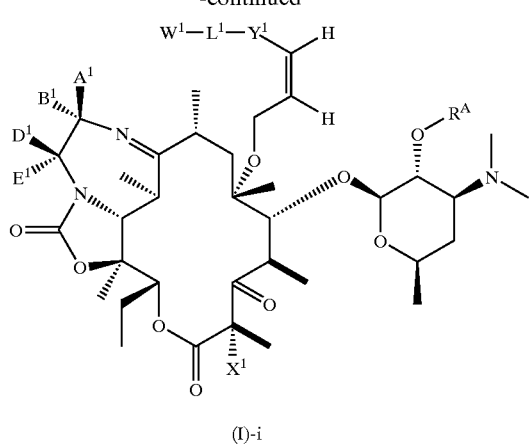

(I)-i

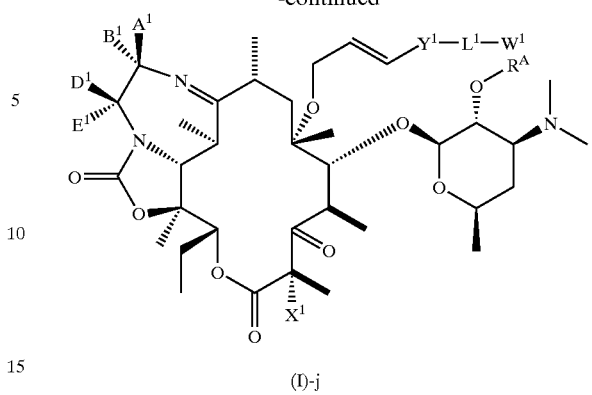

(I)-j

Compounds having formula (I)-h may be converted to compounds having formula (I)-i by reacting the former, hydrogen gas, a hydrogenation catalyst, and, optionally, quinoline. Hydrogenation catalysts include Lindlar catalyst and palladium on barium sulfate. The reaction is typically conducted at 25° C., over about 1 to 6 hours, in solvents such as methanol, ethanol, propanol, butanol, iso-propanol, tert-butanol, acetonitrile, THF, ethyl acetate, and mixtures thereof.

SCHEME 10

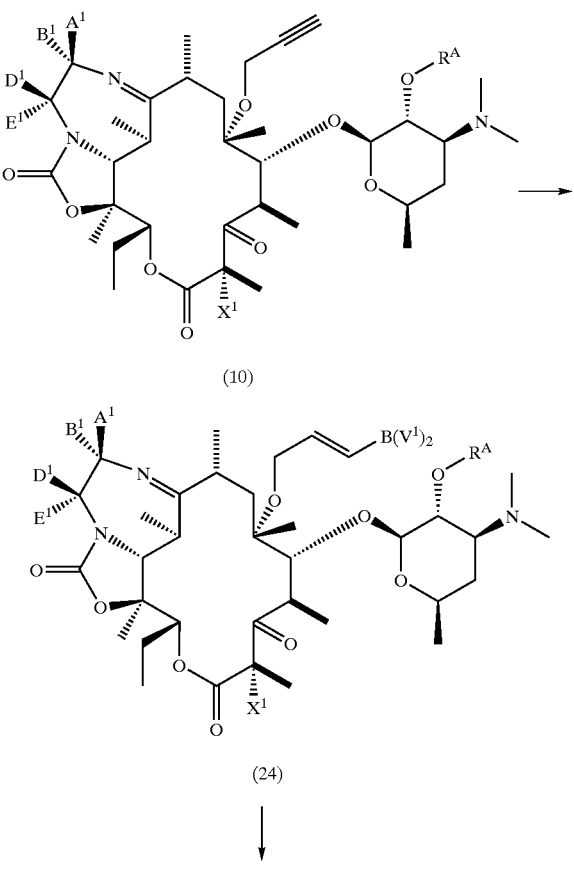

Compounds having formula (10) may be converted to compounds having formula (24) by reacting the former and compounds having formula (23)

$$B(V^1)_3, \qquad (23)$$

in which each $V^1$ is independently hydrogen, alkyl, OH, or $OR^{45}$.

The reaction is typically conducted at about −20° C. to 25° C., over about 1 to 6 hours, in solvents such as THF, DME, and diethyl ether.

Compounds having formula (24) may be converted to compounds having formula (I)-j by reacting the former, compounds having formula (25)

$$X^1\text{-}Y^1\text{-}L^1\text{-}W^1 \qquad (25),$$

a coupling catalyst, a fourth base, and, optionally, a second additive. Coupling catalysts include dichlorobis(triphenylphosphine)palladium(II), tris(dibenzylideneacetone)dipalladium(0), tetrakis(triphenylphosphine)palladium(0), and dichlorobis(triphenylphosphine)nickel(II). Fourth bases include sodium carbonate, sodium bicarbonate, potassium carbonate, cesium carbonate, triethylamine, and diisopropylethylamine. The reaction is typically conducted at about 50° C. to 80° C. over about 12 to 48 hours, in solvents such as acetonitrile, THF, DMF, and DME.

Compounds having formula (I), in which $R^A$ is $R^P$, and $R^P$ is acetyl or benzoyl, may be converted to compounds having formula (I), in which $R^A$ is hydrogen, by reacting the former and methanol. The reaction is typically conducted at about 25° C. to 65° C., over about 2 to 60 hours, in methanol.

Compounds having formula (I), in which $R^A$ is $R^P$, and $R^P$ is trimethylsilyl, may be converted to compounds having formula (I), in which $R^A$ is hydrogen, by reacting the former and a fluoride-donating agent. Fluoride-donating agents include tetrabutylammonium fluoride, polymer-bound ammonium fluoride, tetrabutylammonium fluoride, pyridine.HF, and triethylamine-trihydrofluoride. The reaction is typically conducted at about 0° C. to 50° C., over about 1 to 24 hours, in solvents such as THF and 1,4-dioxane.

The following examples illustrate methods by which certain preferred first embodiments of this invention may be prepared.

EXAMPLE 1

This example was prepared as described in commonly owned U.S. Pat. No. 6,075,133, EXAMPLE 246, step 246c.

EXAMPLE 2

A solution of EXAMPLE 1 (10 g), 4-dimethylaminopyridine (50 mg), benzoic anhydride (7.02 g), and triethylamine (3.8 mL) in dichloromethane (70 mL) at 15° C. was stirred for 20 minutes at 15° C. and at ambient temperature for 7 hours, diluted with ethyl acetate, washed with 5% sodium carbonate, water, and brine, and dried ($Na_2SO_4$), filtered, and concentrated.

EXAMPLE 3

A solution of EXAMPLE 2 (9.80 g), carbonyldiimidazole (4.05 g), and 4-dimethylaminopyridine (122 mg) in THF (45 mL) and DMF (13 mL) was treated with 1,8-diazabicyclo-[5.4.0]undec-7-ene (2.24 mL), stirred at ambient temperature for 12 hours, diluted with ethyl acetate, washed with water and brine, and dried ($Na_2SO_4$), filtered, and concentrated.

EXAMPLE 4

A solution of EXAMPLE 3 (11.09 g) and ethylenediamine (6.67 mL) in acetonitrile (50 mL) and water (5 mL) was stirred at ambient temperature for 3 days and concentrated. The concentrate was dissolved in toluene (140 mL) and acetic acid (7 mL), stirred at 80° C. for 12 hours and at ambient temperature for 12 hours, diluted with dichloromethane, washed with saturated potassium carbonate, and dried ($Na_2SO_4$), filtered, and concentrated; and the concentrate was flash chromatographed on silica gel with 95:5:0.5 dichloromethane/methanol/concentrated ammonium hydroxide.

EXAMPLE 5

A solution of EXAMPLE 4 (5.95 g) and 2M HCl (5 mL) in ethanol (5 mL) was heated to 55° C. for 12 hours and concentrated. The concentrate was dissolved in water, washed with diethyl ether, treated with saturated ammonium hydroxide and extracted with dichloromethane; and the extract was concentrated.

EXAMPLE 6

A solution of N-chlorosuccinimide (5.46 g) in dichloromethane (200 mL) at −10° C. was treated with dimethyl sulfide (3.50 mL), stirred for 10 minutes, treated with a solution of EXAMPLE 5 (20.9 g) in dichloromethane (90 mL) over 30 minutes, stirred for 1 hour, treated with triethylamine (3.79 mL), stirred for 90 minutes, washed with 5% sodium bicarbonate and brine, and dried ($Na_2SO_4$), filtered, and concentrated.

EXAMPLE 7

A solution of EXAMPLE 6 (14 g) in methanol (100 mL) was heated at 60° C. for 16 hours and concentrated; and the concentrate was flash chromatographed on silica gel with 97:2:1 dichloromethane/methanol/concentrated ammonium hydroxide.

EXAMPLE 8

A mixture of EXAMPLE 7 (3.75 g), 5-bromothiophene-2-carboxaldehyde (1.55 g), dichlorobis(triphenylphosphine)-palladium(II) (76 mg), and copper(I) iodide (10.2 mg) in acetonitrile (60 mL) and triethylamine (20 mL) was heated at 75° C. for 14 hours and concentrated; and the concentrate was flash chromatographed on silica gel with 97:2:1 dichloromethane/methanol/concentrated ammonium hydroxide.

EXAMPLE 9

A mixture of EXAMPLE 8 (350 mg), aniline (82.9 μL), and acetic acid (77.8 μL) in methanol (8 mL) was stirred at ambient temperature for 2 hours, treated with sodium cyanoborohydride (57 mg), heated at 60° C. for 1 hour, treated with dichloromethane, washed with 5% sodium bicarbonate and brine, and dried ($Na_2SO_4$), filtered, and concentrated; and the concentrate was flash chromatographed on silica gel with 98:1:1 dichloromethane/methanol/concentrated ammonium hydroxide.

EXAMPLE 10

A mixture of EXAMPLE 8 (280 mg), and O-benzylhydroxylamine hydrochloride (86.6 mg) in methanol (4 mL) was heated at 55° C. for 2 hours, poured into 5% sodium bicarbonate, and extracted with dichloromethane. The extract was washed with brine, dried ($Na_2SO_4$), filtered, and concentrated; and the concentrate was flash chromatographed on silica gel with 97.5:2:0.5 dichloromethane/methanol/concentrated ammonium hydroxide.

EXAMPLE 11

This example was prepared by substituting O-phenylhydroxylamine hydrochloride for O-benzylhydroxylamine hydrochloride in EXAMPLE 8.

EXAMPLE 12

This example was prepared by substituting O-naphthalen-1-ylmethylhydroxylamine and catalytic para-toluenesulfonic acid for O-benzylhydroxylamine hydrochloride in EXAMPLE 8.

EXAMPLE 13

This example was prepared by substituting O-(3-naphthalen-1-yl-allyl)hydroxylamine for O-naphthalen-1-ylmethylhydroxylamine in EXAMPLE 12.

EXAMPLE 14

This example was prepared by substituting O-(2-phenoxy-ethyl)hydroxylamine for O-naphthalen-1-ylmethylhydroxylamine hydrochloride in EXAMPLE 12.

EXAMPLE 15

A mixture of EXAMPLE 7 (350 mg), N-benzyl-N-((5-bromothien-2-yl)methyl)amine (172 mg), dichlorobis-(triphenylphosphine)palladium(II) (7.4 mg), triethylamine (2 mL) and copper(I) iodide (2 mg) in acetonitrile (6 mL) was heated at 80° C. for 20 hours and concentrated; and the concentrate was flash chromatographed on silica gel with 98:1.5:0.5 dichloromethane/methanol/concentrated ammonium hydroxide.

EXAMPLE 16

A mixture of EXAMPLE 8 (200 mg), 2-hydrazinopyridine (42.3 mg), and magnesium sulfate (50 mg) in THF was heated at 66° C. for 16 hours, and filtered. The filtrate was treated with ethyl acetate, washed with water and brine, dried ($Na_2SO_4$), filtered, and concentrated; and the concentrate was flash chromatographed on silica gel with 97.5:2:0.5 dichloromethane/methanol/concentrated ammonium hydroxide.

EXAMPLE 17

This example was prepared by substituting pyridine-2-carbohydrazide for 2-hydrazinopyridine in EXAMPLE 16.

EXAMPLE 18

This example was prepared by substituting O-quinol-3-ylmethylhydroxylamine for O-naphthalen-1-ylmethylhydroxylamine hydrochloride in EXAMPLE 12.

EXAMPLE 19

This example was prepared by substituting N-((5-bromothien-2-yl)methyl)-N-(2-phenylethyl)amine for N-benzyl-N-((5-bromothien-2-yl)methyl)amine in EXAMPLE 15.

EXAMPLE 20

This example was prepared by substituting N-((5-bromothien-2-yl)methyl)-N-(3-phenylpropyl)amine for N-benzyl-N-((5-bromothien-2-yl)methyl)amine in EXAMPLE 15.

EXAMPLE 21

A mixture of EXAMPLE 7 (350 mg), 2-(3-bromophenoxy)pyridine (251 mg), dichlorobis(triphenylphosphine)palladium(II) (11 mg), and copper(I) iodide (1 mg), and triethylamine (2 mL) in acetonitrile (6 mL) was heated at 70° C. for 20 hours and concentrated; and the concentrate was flash chromatographed on silica gel with 98:1.5:0.5 dichloromethane/methanol/concentrated ammonium hydroxide.

EXAMPLE 22

This example was prepared by substituting 5-bromo-N-(3-fluorophenyl)thiophene-2-carboxamide for 2-(3-bromophenoxy)pyridine in EXAMPLE 21.

EXAMPLE 23

This example was prepared by substituting 5-bromo-N-(3-fluorophenyl)-N-methylthiophene-2-carboxamide for 2-(3-bromophenoxy)pyridine in EXAMPLE 21.

EXAMPLE 24

This example was prepared by substituting 1-bromo-3-(3-fluorophenoxy)benzene for 2-(3-bromophenoxy)pyridine in EXAMPLE 21.

EXAMPLE 25

A solution of EXAMPLE 6 (5 g), 2,5-dibromothiophene (4.74 g), dichlorobis(triphenylphosphine)palladium(II) (184 mg), and copper(I) iodide (17 mg), and triethylamine (9 mL) in acetonitrile (27 mL) was heated at 80° C. for 24 hours, concentrated, treated with dichloromethane, washed with 5% sodium bicarbonate and brine, dried ($Na_2SO_4$), filtered, and concentrated; and the concentrate was flash chromatographed on silica gel with 98.5:1:0.5 dichloromethane/methanol/concentrated ammonium hydroxide.

EXAMPLE 26

A solution of EXAMPLE 25, (300 mg), 2-ethynylpyridine (41.7 mg), dichlorobis(triphenylphosphine)palladium(II) (4.5 mg), copper(I) iodide (0.6 mg) and triethylamine (1 mL) in acetonitrile (3 mL) was heated at 75° C. for 14 hours and concentrated.

EXAMPLE 26A

A solution of EXAMPLE 26 in methanol (10 mL) was heated at 60° C. for 14 hours and concentrated; and the concentrate was flash chromatographed on silica gel with 98:1:1 dichloromethane/methanol/concentrated ammonium hydroxide.

EXAMPLE 27

This example was prepared by substituting 1-bromo-4-phenoxybenzene for 2-(3-bromophenoxy)pyridine in EXAMPLE 21.

EXAMPLE 28

This example was prepared by substituting 5-bromo-N-pyridin-3-ylthiophene-2-carboxamide for 2-(3-bromophenoxy)pyridine in EXAMPLE 21.

EXAMPLE 29

This example was prepared by substituting 5-bromo-N-(4-(1,2,3-thiadiazol-4-yl)benzyl)thiophene-2-carboxamide for 2-(3-bromophenoxy)pyridine in EXAMPLE 21.

EXAMPLE 30

This example was prepared by substituting 5-bromo-N-(3-(quinolin-3-yl)propyl)thiophene-2-carboxamide for 2-(3-bromophenoxy)pyridine in EXAMPLE 21.

EXAMPLE 31

This example was prepared by substituting N-benzyl-N-((5-bromothien-2-yl)methyl)-N-methylamine for 2-(3-bromophenoxy)pyridine in EXAMPLE 21.

EXAMPLE 32

A mixture of EXAMPLE 7, (300 mg), N-(3-bromophenyl)-N'-pyridin-4-ylurea (123 mg), tris(dibenzylideneacetone)-dipalladium(0) (16.6 mg), 1,2-bis(diphenylphosphino)ethane (14.4 mg), triethylamine (1.5 mL), and copper(I) iodide (0.86 mg) in acetonitrile (5 mL) was heated at 75° C. for 18 hours and concentrated; and the concentrate was flash chromatographed on silica gel with 98:1:1 dichloromethane/methanol/concentrated ammonium hydroxide.

EXAMPLE 33

A solution of EXAMPLE 6 (672 mg) in DMF (5 mL) at 0° C. was treated with 60% oily sodium hydride (70 mg), stirred for 40 minutes, treated with N-fluorobenzenesulphonimide (314 mg), stirred for 3 hours, diluted with ethyl acetate, washed with water and brine, dried ($Na_2SO_4$), filtered, and concentrated; and the concentrate was flash chromatographed on silica gel with 95:5:0.5 dichloromethane/methanol/concentrated ammonium hydroxide.

Spectral Data for Representative Compounds

EXAMPLE 7

$^{13}C$ NMR ($CDCl_3$) δ 204.7, 169.5, 156.0, 103.4, 81.59, 81.53, 80.36, 77.2 (C-5), 77.2 (C-13), 74.3, 70.26, 69.6, 65.9, 60.1, 51.1, 50.6, 49.3, 47.1, 42.6, 42.2, 40.2, 40.2, 37.9, 36.3, 28.3, 22.3, 21.2, 20.3, 19.6, 15.0, 14.5, 12.9, 11.0, 10.6.

EXAMPLE 10

$^{13}C$ NMR ($CDCl_3$) δ 204.88, 204.85, 179.86, 179.80, 169.56, 169.53, 156.0, 143.16, 140.37, 132.18, 131.31, 131.28, 128.95, 128.45, 128.42, 128.02, 127.93, 103.60, 103.56, 93.97, 93.34, 81.48, 80.43, 78.94, 77.45, 77.34, 77.29, 76.87, 76.71, 70.32, 69.64, 65.89, 60.25, 51.41, 51.20, 49.47, 47.40, 47.32, 42.71, 42.28, 40.24, 37.99, 36.29, 28.20, 22.29, 21.25, 20.26, 19.65, 15.39, 15.28, 14.57, 13.03, 11.09, 10.53.

EXAMPLE 11

$^{13}$C NMR (CDCl$_3$) δ 204.86, 180.02, 179.94, 169.62, 169.59, 156.00, 145.61, 142.32, 132.54, 132.29, 131.39, 131.36, 130.40, 129.33, 129.29, 122.86, 122.41, 114.91, 114.42, 103.60, 103.54, 94.59, 93.88, 81.51, 80.49, 78.74, 77.43, 77.40, 77.28, 70.30, 69.66, 65.87, 51.45, 51.39, 51.20, 49.50, 49.47, 47.40, 47.29, 42.73, 42.28, 40.24, 38.02, 37.99, 36.31, 28.20, 22.27, 21.25, 20.26, 20.22, 19.65, 15.36, 15.23, 14.60, 13.03, 11.08, 10.53.

EXAMPLE 12

$^{13}$C NMR (CDCl$_3$) δ 204.87, 204.83, 179.76, 179.73, 169.52, 156.0, 143.19, 140.19, 136.79, 133.72, 132.18, 131.86, 131.31, 131.28, 129.11, 129.01, 128.53, 128.49, 127.62, 127.12, 126.35, 125.78, 125.26, 124.11, 123.99, 103.60, 103.54, 93.92, 93.37, 81.48, 81.43, 80.45, 80.41, 78.94, 78.89, 77.45, 77.32, 77.307, 75.41, 75.08, 70.30, 69.64, 65.87, 60.23, 51.39, 51.20, 51.17, 49.47, 49.39, 47.40, 47.29, 42.69, 42.28, 42.23, 40.22, 37.96, 36.29, 28.19, 22.27, 21.24, 20.26, 19.64, 15.39, 15.23, 14.55, 13.023, 11.06, 10.51.

EXAMPLE 13

$^{13}$C NMR (CDCl$_3$) δ 204.89, 204.85, 179.79, 169.45, 156.0, 155.97, 143.19, 143.15, 140.29, 132.19, 131.33, 131.28, 130.90, 130.45, 128.98, 128.43, 128.16, 128.06, 128.12, 128.09, 126.05, 125.73, 125.69, 125.57, 124.08, 123.89, 123.85, 103.60, 103.54, 93.88, 93.37, 81.48, 80.46, 80.39, 79.0, 77.45, 77.34, 77.27, 77.29, 75.71, 75.30, 70.30, 69.64, 65.89, 60.25, 51.41, 51.22, 51.17, 49.49, 49.41, 47.42, 47.32, 42.69, 42.28, 40.22, 38.00, 36.29, 28.20, 22.32, 22.27, 21.24, 20.28, 19.63, 15.39, 15.25, 14.57, 13.06, 13.04, 11.08, 10.56.

EXAMPLE 14

$^{13}$C NMR (CDCl$_3$) δ 204.89, 204.85, 179.86, 179.80, 169.56, 169.45, 156.0, 155.97, 143.57, 140.48, 132.21, 131.87, 131.37, 131.33, 129.40, 129.16, 120.89, 114.81, 114.70, 103.62, 103.57, 93.92, 93.42, 81.48, 80.46, 80.39, 78.89, 77.43, 77.36, 77.31, 77.28, 73.12, 72.84, 70.30, 69.66, 66.23, 65.91, 60.25, 51.41, 51.22, 51.19, 49.49, 49.43, 47.44, 47.37, 42.69, 42.27, 40.24, 37.99, 36.29, 28.20, 22.32, 22.27, 21.25, 20.226, 19.63, 15.43, 15.29, 14.56, 13.06, 13.04, 11.08, 10.56.

EXAMPLE 15

$^{13}$C NMR (CDCl$_3$) δ 204.9, 179.8, 169.6, 156.0, 146.4, 139.8, 132.1, 128.4, 128.4, 128.1, 128.1, 126.9, 124.6, 121.5, 103.5, 90.9, 81.5, 80.2, 79.4, 77.4, 77.3 70.3, 69.6, 65.9, 60.2, 52.6, 51.4, 51.2, 49.4, 47.6, 47.4, 42.7, 42.2, 40.2, 38.0, 36.2, 28.2, 22.3.

EXAMPLE 16

$^{13}$C NMR (CDCl$_3$) δ 204.88, 204.85, 180.04, 179.83, 169.51, 169.48, 156.0, 147.61, 147.63, 138.15, 138.09, 137.97, 133.00, 132.54, 130.40, 129.30, 126.78, 116.67, 115.23, 107.94, 107.96, 103.57, 94.34, 93.03, 81.53, 81.49, 80.48, 80.38, 79.28, 78.28, 77.40, 77.31, 70.30, 69.64, 65.88, 60.23, 51.39, 51.20, 49.47, 47.40, 42.68, 42.26, 40.22, 37.99, 36.28, 28.20, 25.23, 22.29, 21.25, 20.28, 20.25, 19.62, 15.39, 15.35, 14.55, 13.04, 11.08, 10.54.

EXAMPLE 17

$^{13}$C NMR (CDCl$_3$) δ 204.91, 180.07, 169.39, 156.10, 132.67, 103.59, 81.66, 80.43, 77.36, 77.28, 70.32, 69.66, 65.87, 60.26, 51.39, 51.19, 49.39, 47.42, 42.65, 42.24, 40.24, 38.00, 36.23, 28.20, 22.35, 21.25, 20.26, 19.60, 15.38, 14.54, 13.08, 11.09, 10.59.

EXAMPLE 18

$^{13}$C NMR (CDCl$_3$) δ 204.91, 204.85, 179.99, 179.83, 169.54, 169.37, 156.0, 155.97, 151.07, 150.89, 147.88, 143.78, 140.85, 136.39, 135.66, 135.42, 132.22, 131.65, 131.44, 130.21, 130.00, 129.53, 129.47, 129.32, 129.29, 128.02, 127.95, 126.77, 126.72, 103.61, 103.54, 94.03, 93.51, 81.51, 80.46, 80.39, 78.86, 77.39, 77.28, 77.19, 77.21, 74.46, 74.15, 70.30, 69.64, 65.89, 60.23, 51.39, 51.20, 51.16, 49.47, 49.42, 47.42, 47.34, 42.69, 42.26, 42.23, 40.24, 38.00, 37.97, 36.28, 28.20, 22.36, 22.29, 21.24, 20.28, 20.23, 19.63, 15.41, 15.25, 14.54, 13.10, 13.04, 11.09, 10.58.

EXAMPLE 19

$^{13}$C NMR (CDCl$_3$) δ 204.9, 179.8, 169.6, 156.0, 146.4, 139.8, 132.1, 128.4, 128.4, 128.1, 128.1, 126.9, 124.6, 121.5, 103.5, 90.9, 81.5, 80.2, 79.4, 77.4, 77.3 70.3, 69.6, 65.9, 60.2, 52.6, 51.4, 51.2, 49.4, 47.6, 47.4, 42.7, 42.2, 40.2, 38.0, 36.2, 28.2, 22.3.

EXAMPLE 20

$^{13}$C NMR (CDCl$_3$) δ 204.9, 179.8, 169.3, 156.0, 146.6, 142.1, 132.1, 128.4 128.3, 125.7, 124.5, 121.5, 103.6, 91.0, 81.5, 80.2, 79.4, 77.4, 77.3, 70.3, 69.7, 69.6, 65.9, 60.2, 51.4, 51.2, 49.4, 48.5, 48.5, 47.4, 42.7, 42.2, 40.2, 38.0, 36.2, 33.5, 31.6, 28.2, 22.3, 21.2, 20.3, 19.6, 15.4, 14.5, 13.1, 11.1.

EXAMPLE 21

$^{13}$C NMR (CDCl$_3$) δ 204.8, 180.1, 169.6, 163.4, 155.9, 153.9, 147.7, 139.4, 129.5, 127.8, 124.4, 124.0, 121.3, 118.6, 111.5, 103.5, 88.1, 84.9, 81.4, 80.3, 77.5, 77.1, 70.2, 69.5, 65.9, 60.2, 51.3, 51.2, 49.3, 47.2, 42.6, 41.2, 40.2, 38.0, 36.2, 28.3, 22.2, 21.2, 20.2, 19.6, 15.2, 14.6, 13.0, 11.0, 10.4.

EXAMPLE 22

$^{13}$C NMR (CDCl$_3$) δ 205.0, 180.6, 169.2, 164.5, 159.2, 156.3, 139.4, 139.3, 138.8, 132.7, 130.1, 129.9, 129.4, 127.6, 115.5, 115.5, 111.3, 111.0, 107.8, 107.5, 103.6, 93.7, 81.8, 80.4, 78.5, 77.7, 77.1, 72.2, 70.2, 69.6, 65.9, 60.3, 51.3, 51.2, 49.3, 47.6, 42.6, 42.4, 40.2 38.1, 36.1, 28.2, 22.5, 21.2, 20.3, 19.6, 15.6, 13.2, 11.2, 10.7.

EXAMPLE 23

$^{13}$C NMR (CDCl$_3$) δ 204.8, 179.7, 169.6, 164.7, 161.8, 155.9, 145.3, 145.2, 137.7, 132.3, 131.5, 131.1, 127.9, 123.9, 115.7, 115.5, 115.4, 115.3, 103.6, 93.7, 81.4, 80.4, 78.3, 77.4, 77.2, 70.3, 69.6, 65.9, 60.1, 51.3, 51.2, 49.4, 47.3, 42.6, 42.2, 40.2, 38.9, 37.9, 36.2, 28.1, 22.2, 21.2, 20.2, 19.6, 15.3, 14.5, 12.9, 11.0, 10.5.

EXAMPLE 24

$^{13}$C NMR (CDCl$_3$) δ 204.9, 179.8, 169.6, 160.5, 157.5, 156.0, 129.6, 126.3, 124.5, 121.0, 120.8, 120.7, 118.8, 118.4, 116.5, 116.2, 103.5, 88.0, 84.9, 81.5, 80.3, 77.4, 77.2, 70.3, 69.6, 65.9, 60.2, 51.3, 51.2, 49.4, 47.2, 42.7, 42.2, 40.2, 38.0, 36.3, 28.2, 22.3, 21.2, 20.2, 19.6, 15.2, 14.6, 13.0, 11.1, 10.5.

EXAMPLE 25

$^{13}$C NMR (100 MHz, CDCl$_3$) δ 204.9, 179.9, 169.6, 156.0, 150.1, 142.9, 136.1, 133.0, 132.1, 127.1, 125.3, 123.4, 122.9, 103.6, 92.9, 92.8, 82.2, 81.5, 80.5, 78.6, 77.4, 77.3, 70.3, 69.7, 65.9, 60.2, 51.4, 51.2, 49.5, 47.3, 42.7, 42.3, 40.2, 38.0, 36.3, 28.2, 22.3, 21.2, 20.2, 19.7, 15.3, 14.6, 13.0, 11.0, 10.5.

EXAMPLE 27

$^{13}$C NMR (CDCl$_3$) δ 204.9, 179.9, 169.5, 157.4, 156.0, 133.1, 129.8, 123.7, 119.3, 118.8, 118.3, 117.6, 103.5, 86.7, 85.1, 81.5, 80.2, 77.4, 77.3, 70.3, 69.6, 65.9, 60.2, 51.4, 51.2, 49.4, 47.3, 42.7, 42.2, 40.2, 38.1, 36.3, 28.2, 22.3, 21.2, 20.2, 19.6, 15.3, 14.6, 13.1, 11.1, 10.6.

EXAMPLE 28

$^{13}$C NMR (CDCl$_3$) δ 204.9, 180.3, 169.1, 159.7, 156.3, 145.2, 141.7, 138.8, 135.0, 132.6, 129.4, 127.9, 127.7, 123.6, 103.6, 93.8, 81.8, 80.4, 78.4, 77.6, 77.1, 70.3, 69.6, 65.8, 60.3, 57.3, 51.2, 49.3, 47.5, 42.6, 42.3, 40.2, 38.0, 36.1, 28.2, 22.4, 21.2, 20.3, 19.5, 15.5, 14.5, 13.1, 11.2, 10.6.

EXAMPLE 29

$^{13}$C NMR (CDCl$_3$) δ 204.8, 180.0, 169.4, 162.4, 161.1, 156.1, 139.4, 138.8, 132.5, 130.0, 128.5, 128.5, 127.7, 127.1, 103.6, 93.5, 81.6, 80.4, 78.4, 77.4, 77.3, 70.3, 69.6, 65.8, 60.2, 51.3, 51.2, 49.4, 47.4, 43.6, 42.6, 42.2, 40.2, 38.0, 36.2, 28.2, 22.3, 21.2, 20.2, 19.6, 15.4, 14.5, 11.1, 10.6.

EXAMPLE 30

$^{13}$C NMR (CDCl$_3$) δ 204.9, 180.2, 169.3, 161.2, 156.1, 151.7, 146.9, 138.9, 134.3, 134.0, 132.5, 129.1, 128.7, 128.4, 128.1, 127.4, 126.6, 103.6, 93.3, 81.7, 80.4, 78.5, 77.6, 77.2, 70.3, 69.6, 65.9, 60.3, 51.3, 51.2, 49.4, 47.5, 42.6, 42.3, 40.2, 39.6, 38.0, 36.2, 30.9, 30.5, 28.2, 22.4, 21.2, 20.3, 19.6, 15.5, 14.5, 13.1, 11.1, 10.6.

EXAMPLE 31

$^{13}$C NMR (CDCl$_3$) δ 204.8, 179.7, 169.4, 156.0, 145.1, 138.8, 131.9, 128.8, 128.2, 127.0, 125.2, 122.0, 103.5, 91.0, 81.5, 80.2, 79.5, 77.3, 77.3, 70.3, 69.6, 65.9, 61.1, 60.2, 56.0, 51.4, 51.2, 49.4, 47.3, 42.7, 42.3, 42.0, 40.2, 38.0, 36.2, 28.2, 22.3, 21.2, 20.2, 19.6, 15.3, 14.5, 13.0, 11.1, 10.5.

EXAMPLE 32

$^{13}$C NMR (CDCl$_3$) δ 205.3, 180.7, 169.1, 156.7, 152.1, 150.1, 146.8, 138.6, 129.2, 126.3, 123.3, 121.8, 119.5, 112.9, 103.9, 87.0, 85.5, 82.3, 80.3, 77.7, 77.6, 70.4, 69.7, 65.8, 60.5, 51.3, 51.3, 49.1, 47.5, 42.5, 42.3, 40.2, 38.2, 36.1, 28.1, 22.6, 21.2, 20.1, 19.5, 15.5, 14.7, 13.2, 11.2, 10.7.

The foregoing is merely illustrative of this invention and is not intended to limit the same to the disclosed compounds. Variations and changes which are obvious to one skilled in the art are intended to be within the scope and nature of this invention which is defined in the appended claims.

What is claimed is:

1. A compound, or salt, prodrug, or salt of a prodrug thereof, having formula (I)

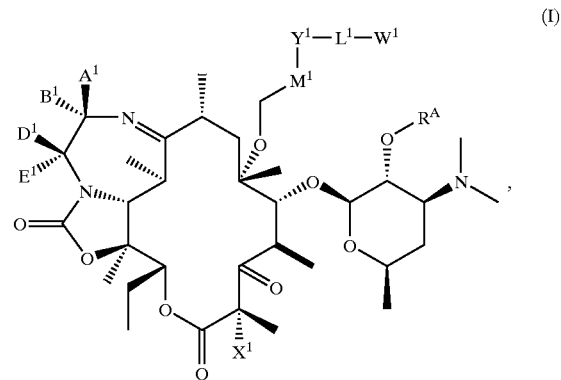

in which two of $A^1$, $B^1$, $D^1$, and $E^1$ are hydrogen, alkyl, alkenyl, alkynyl, cycloalkyl, aryl, heteroaryl, heterocyclyl, —CN, —OH, —SH, —C(O)H, —C(O)R$^1$, —C(O)OH, —C(O)OR$^1$, —C(O)NR$^2$R$^3$, or alkyl substituted by one, two, or three substituents independently selected from the group consisting of —CN, —OH, —SH, halo, aryl, heteroaryl, heterocyclyl, —OR$^1$, —SR$^1$, —C(O)H, —C(O)R$^1$, —C(O)OH, —C(O)OR$^1$, —CH═N—OR$^1$, —OC(O)R$^1$, —OC(O)OR$^1$, —C(O)NR$^2$R$^3$, —OC(O)NR$^2$R$^2$, —NR$^2$R$^3$, —N(R$^4$)C(O)H, —N(R$^4$)C(O)R$^1$, —N(R$^4$)C(O)NR$^2$R$^3$, —N(R$^4$)SO$_2$R$^1$, —OR$^1$, —SR$^1$, —S(O)R$^1$, —SO$_2$R$^1$, and —SO$_2$NR$^2$R$^3$, and the remainder are hydrogen; or $A^1$ and $D^1$, $A^1$ and $E^1$, $B^1$ and $D^1$, or $B^1$ and $D^1$ together are one- to five-membered alkylene or two- to five-membered heteroalkylene, and the remainder are hydrogen; or $A^1$ and $B^1$ together are one- to seven-membered alkylene or two- to seven-membered heteroalkylene, and $D^1$ and $E^1$ are hydrogen; or $D^1$ and $E^1$ together are one- to seven-membered alkylene or two- to seven-membered heteroalkylene, and $A^1$ and $B^1$ are hydrogen;

$X^1$ is hydrogen or fluoride;

$M^1$ is (E)—CH═CH, (Z)—CH═CH, or C≡C;

$Y^1$ is arylene or heteroarylene;

$L^1$ is drawn from left to right and is alkylene, alkenylene, alkynylene, CH═N—O—CH$_2$-(alkenylene), CH$_2$N(R$^5$), CH$_2$N(R$^5$)(CH$_2$)$_m$, C(O)N(R$^5$), N(R$^5$)C(O)N(R$^6$), CH═N—N(R$^5$), CH═N—N(R$^5$)C(O), O, CH═N—O, CH═N—O—(CH$_2$)m, C(O)N(R$^5$)(CH$_2$)$_m$, or CH═N—O(CH$_2$)$_n$—O, in which m is one, two, three, or four, and n is two, three, or four;

$W^1$ is hydrogen, aryl, heteroaryl, or heterocyclyl;

$R^1$ is alkyl, aryl, heteroaryl, or heterocyclyl;

$R^2$ and $R^3$ are independently hydrogen or alkyl; or $R^2$ and $R^3$ together are 3- to 7-membered alkylene or 3-to 7-membered heteroalkylene;

$R^4$ is hydrogen or alkyl;

$R^5$ and $R^6$ are independently hydrogen or alkyl; and $R^A$ is hydrogen or $R^P$ in which $R^P$ is a hydroxyl protecting moiety;

in which, for the foregoing, each aryl, arylene, heteroaryl, heteroarylene, heterocyclyl, and heterocycloalkylene is unsubstituted or substituted by one, two, three, four, or five substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, SR$^{30}$, —S(O)R$^{35}$, —SO$_2$R$^{35}$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH (R$^{35}$), —C(O)N(R$^{35}$)(R$^{36}$), —OC(O)R$^{35}$, —OC(O) OR$^{35}$, —OC(O)NH$_2$, —OC(O)NH(R$^{35}$), —OC(O)N (R$^{35}$)(R$^{36}$), —NHC(O)H, —NHC(O)R$^{35}$, —NHC(O) OR$^{35}$, —NHC(O)NH$_2$, —NHC(O)NH(R$^{35}$), —NHC (O)N(R$^{35}$)(R$^{36}$), —SO$_2$NH$_2$, —SO$_2$NH(R$^{35}$), —SO$_2$N (R$^{35}$) (R$^{36}$), R$^{40}$ and alkyl substituted with one or two substituents independently selected from the group consisting of halo, —CN, —OH, —SH, =O, —OR$^{30}$, —SR$^{30}$, —C(O)OH, —C(O)OR$^{35}$, —NH$_2$, —NH (R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —OC(O)NH(R$^{35}$), —OC(O)N(R$^{35}$)(R$^{36}$), —SO$_2$NH$_2$, —SO$_2$NH(R$^{35}$), —SO$_2$N(R$^{35}$)(R$^{36}$) and R$^{40}$;

R$^{30}$ is alkyl or alkyl substituted with a substituent selected from the group consisting of halo and —OR$^{45}$;

R$^{35}$ and R$^{36}$ are independently selected alkyl;

R$^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, tetrazolyl, pyridyl, pyrazinyl, pyrimidinyl, pyrrolidinyl, inidazolidinyl, piperidinyl, piperazinyl, morpholinyl, or thiomorpholinyl, each of which is unsubstituted or substituted with one, two, or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{45}$, —SR$^{45}$, —S(O) R$^{50}$, —SO$_2$R$^{50}$, —C(O)H, —C(O)R$^{50}$, —C(O)OH, —C(O)OR$^{50}$, —NH$_2$, —NH(R$^{50}$), —N(R$^{50}$)(R$^{51}$), —C(O)NH$_2$, —C(O)NH(R$^{50}$), —C(O)N(R$^{50}$)(R$^{51}$), —OC(O)R$^{50}$, —OC(O)OR$^{50}$, —OC(O)NH$_2$, —OC(O) NH(R$^{50}$), —OC(O)N(R$^{50}$)(R$^{51}$), —NHC(O)H, —NHC (O)R$^{50}$, —NHC(O)OR$^{50}$, —NHC(O)NH$_2$, —NHC(O) NH(R$^{50}$), —NHC(O)N(R$^{50}$)(R$^{51}$), —SO$_2$NH$_2$, SO$_2$NH (R$^{50}$), and —SO$_2$N(R$^{50}$)(R$^{51}$);

R$^{45}$ is alkyl; and

R$^{50}$ and R$^{51}$ are independently selected alkyl.

2. A compound of claim 1 in which A$^1$, B$^1$, D$^1$, and E$^1$ are hydrogen; X$^1$ is hydrogen; M$^1$ is C≡C; Y$^1$ is arylene or heteroarylene, in which the Y$^1$ arylene is 1,3-phenylene or 1,4-phenylene, and in which the Y$^1$ heteroarylene is 2,5-thienylene; L$^1$ is drawn from left to right and is alkynylene, CH=N—O—CH$_2$-(alkenylene), CH$_2$N(R$^5$), CH$_2$N(R$^5$)(CH$_2$)$_m$, C(O)N(R$^5$), N(R$^5$)C(O)N(R$^6$), CH=N—N(R$^5$), CH=N—N(R$^5$)C(O), O, CH=N—O, CH=N—O(CH$_2$)$_m$, C(O)N(R$^5$)(CH$_2$)$_m$, or CH=N—O(CH$_2$)$_n$—O, in which m is one, two, or three; and n is three; W$^1$ is hydrogen, aryl, or heteroaryl, in which the aryl is phenyl or phenyl fused with another phenyl (naphthyl), each of which is unsubstituted or substituted by one substituent selected from the group consisting of halo and R$^{40}$, in which R$^{40}$ is 1,2,3-thiadiazolyl, and in which the heteroaryl is pyridyl or pyridyl fused with phenyl (quinolinyl); with the proviso that W$^1$ is hydrogen only when L$^1$ is CH=N—O(CH$_2$)$_m$; R$^5$ is hydrogen or alkyl; R$^6$ is hydrogen; and R$^A$ is hydrogen.

3. A compound of claim 1 in which A$^1$, B$^1$, D$^1$, and E$^1$ are hydrogen; X$^1$ is hydrogen; M$^1$ is C≡C; Y$^1$ is arylene or heteroarylene, in which the arylene is 1,3-phenylene or 1,4-phenylene, and in which the heteroarylene is 2,5-thienylene; L$^1$ is drawn from left to right and is C$_2$-alkynylene, CH=N—O—CH$_2$—(C$_2$-alkenylene), CH$_2$N(R$^5$), CH$_2$N(R$^5$)(CH$_2$)$_m$, C(O)N(R$^5$), N(R$^5$)C(O)N (R$^6$), CH=N—N(R$^5$), CH=N—N(R$^5$)C(O), O, CH=N—O, CH=N—O(CH$_2$)$_m$, C(O)N(R$^5$)(CH$_2$)$_m$, or CH=N—O (CH$_2$)$_n$—O, in which m is one, two, or three, and n is three; W$^1$ is hydrogen, aryl, heteroaryl, or heterocyclyl, in which the aryl is phenyl or phenyl fused with another phenyl (naphthyl), each of which is unsubstituted or substituted by one substituent selected from the group consisting of halo and R$^{40}$, in which R$^{40}$ is 1,2,3-thiadiazolyl, and in which the heteroaryl is pyridyl or pyridyl fused with phenyl (quinolinyl); with the proviso that W$^1$ is hydrogen only when L$^1$ is CH=N—O(CH$_2$)$_m$ and m is one; R$^5$ is hydrogen or C$_1$-alkyl; R$^6$ is hydrogen; and R$^A$ is hydrogen.

4. A composition for treatment of bacterial infections in a fish or a mammal, the composition comprising a therapeutically effective amount of a compound of claim 1.

5. A method treatment of bacterial infections in a fish or a mammal comprising administering thereto a therapeutically effective amount of a compound of claim 1.

6. A compound of claim 1 which is (2R,4R,5R,6R,8R,11R,12S,19R,20R)-11-ethyl-2,4,6,8,12,19-hexamethyl-7,9,14-trioxo-4-(3-(5-((phenylamino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-(((phenylmethyl)oxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-((methyloxy)imino)methyl)thien-2-yl)prop-2-ynyl)-7,9, 14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-((phenyloxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-(((naphthalen-1-ylmethyl)oxy)imino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-4-(3-(5-((E)-(((3-naphthalen-1-ylprop-2-enyl)oxy)imino)methyl)thien-2-yl)prop-2-ynyl)-7,9,14-trioxo-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,12,19-hexamethyl-7,9,14-trioxo-4-(3-(5-((E)-(((2-(phenyloxy)ethyl)oxy)imino)methyl)thien-2-yl)prop-2-ynyl)-10,13-dioxa-15,18-diazatricyclo[10.6.2.0$^{15,20}$]icos-1(18)-en-5-yl 3,4,6-trideoxy-3-(dimethylamino)-β-D-xylo-hexopyranoside, (2R,4R,5R,6R,8R,11R,12S,19R,20R)-11-ethyl-2,4,6,8,
12,19-hexamethyl-7,9,14-trioxo-4-(3-(5-
(((phenylmethyl)amino)methyl)thien-2-yl)prop-2-
ynyl)-10,13-dioxa-15,18-diazatricyclo[10.6.2.0$^{15,20}$]
icos-1(18)-en-5-yl 3,4,6-trideoxy-3-(dimethylamino)-
β-D-xylo-hexopyranoside, (2R,4R,5R,6R,8R,11R,12S,19R,20R)-11-ethyl-2,4,6,8,
12,19-hexamethyl-7,9,14-trioxo-4-(3-(5-((E)-(pyridin-
2-ylhydrazono)methyl)thien-2-yl)prop-2-ynyl)-10,13-
50 dioxa-15,18-diazatricyclo[10.6.2.0$^{15,20}$]icos-1(18)-
en-5-yl 3,4,6-trideoxy-3-(dimethylamino)-β-D-xylo-
hexopyranoside, N'-((1E)-(5-(3-((2R,4R,5R,6R,8R,11R,12S,19R,20R)-11-
ethyl-2,4,6,8,12,19-hexamethyl-7,9,14-trioxo-5-((3,4,
6-trideoxy-3-(dimethylamino)-β-D-xylo-
hexopyranosyl)oxy)-10,13-dioxa-15,18-diazatricyclo
[10.6.2.0$^{15,20}$]icos-1(18)-en-4-yl)prop-1-ynyl)thien-2-
yl)methylidene)pyridine-2-carbohydrazide, (2R,4R,5R,6R,8R,11R,12S,19R,20R)-11-ethyl-2,4,6,8,
12,19-hexamethyl-7,9,14-trioxo-4-(3-(5-((E)-60
(((quinolin-3-ylmethyl)oxy)imino)methyl)thien-2-yl)
prop-2-ynyl)-10,13-dioxa-15,18-diazatricyclo
[10.6.2.0$^{15,20}$]icos-1(18)-en-5-yl 3,4,6-trideoxy-3-
(dimethylamino)-β-D-xylo-hexopyranoside, (2R,4R,5R,6R,8R,11R,12S,19R,20R)-11-ethyl-2,4,6,8,
12,19-hexamethyl-7,9,14-trioxo-4-(3-(5-(((2-
phenylethyl)amino)methyl)thien-2-yl)prop-2-ynyl)-10,
13-dioxa-15,18-diazatricyclo[10.6.2.0$^{15,20}$]icos-1(18)-
en-5-yl 3,4,6-trideoxy-3-(dimethylamino)-β-D-xylo-
hexopyranoside, (2R,4R,5R,6R,8R,11R,12S,19R,20R)-11-ethyl-2,4,6,8,
12,19-hexamethyl-7,9,14-trioxo-4-(3-(5-(((3-
phenylpropyl)amino)methyl)thien-2-yl)prop-2-ynyl)-
10, 13-dioxa-15,18-diazatricyclo[10.6.2.0$^{15,20}$]icos-1
(18)-en-5-yl 3,4,6-trideoxy-3-(dimethylamino)-β-D-
xylo-hexopyranoside, (2R,4R,5R,6R,8R,11R,12S,19R,20R)-11-ethyl-2,4,6,8,
12,19-hexamethyl-7,9,14-trioxo-4-(3-(3-(pyridin-2-
yloxy)phenyl)prop-2-ynyl)-10,13-dioxa-15,
18-diazatricyclo[10.6.2.0$^{15,20}$]icos-1(18)-en-5-yl 3,4,
6-trideoxy-3-(dimethylamino)-β-D-xylo-
hexopyranoside, 5-(3-((2R,4R,5R,6R,8R,11R,12S,19R,20R)-11-ethyl-2,4,
6,8,12,19-hexamethyl-7,9,14-trioxo-5-((3,4,6-
trideoxy-3-(dimethylamino)-β-D-xylo-hexopyranosyl)
oxy)-10,13-dioxa-15,18-diazatricyclo[10.6.2.0$^{15,20}$]
icos-1(18)-en-4-yl)prop-1-ynyl)-N-(3-fluorophenyl)
thiophene-2-carboxamide, 5-(3-((2R,4R,5R,6R,8R,11R,12S,19R,20R)-11-ethyl-2,4,
6,8,12,19-hexamethyl-7,9,14-trioxo-5-((3,4,6-
trideoxy-3-(dimethylamino)-β-D-xylo-hexopyranosyl)
oxy)-10,13-dioxa-15,18-diazatricyclo[10.6.2.0$^{15,20}$]
icos-1(18)-en-4-yl)prop-1-ynyl)-N-(3-fluorophenyl)-
N-methylthiophene-2-carboxamide, (2R,4R,5R,6R,8R,11R,12S,19R,20R)-11-ethyl-4-(3-(3-
((3-fluorophenyl)oxy)phenyl)prop-2-ynyl)-2,4,6,8,12,
19-hexamethyl-7,9,14-trioxo-10,13-dioxa-15,
18-diazatricyclo[10.6.2.0$^{15,20}$]icos-1(18)-en-5-yl 3,4,
6-trideoxy-3-(dimethylamino)-β-D-xylo-
hexopyranoside, (2R,4R,5R,6R,8R,11R,12S,19R,20R)-11-ethyl-2,4,6,8,
12,19-hexamethyl-7,9,14-trioxo-4-(3-(5-(pyridin-2-
ylethynyl)thien-2-yl)prop-2-ynyl)-10,13-dioxa-15,
18-diazatricyclo[10.6.2.0$^{15,20}$]icos-1(18)-en-5-yl 3,4,
6-trideoxy-3-(dimethylamino)-β-D-xylo-
hexopyranoside, (2R,4R,5R,6R,8R,11R,12S,19R,20R)-11-ethyl-2,4,6,8,
12,19-hexamethyl-7,9,14-trioxo-4-(3-(4-(phenyloxy)
phenyl)prop-2-ynyl)-10,13-dioxa-15,18-diazatricyclo
[10.6.2.0$^{15,20}$]icos-1(18)-en-5-yl 3,4,6-trideoxy-3-
(dimethylamino)-β-D-xylo-hexopyranoside, 5-(3-((2R,4R,5R,6R,8R,11R,12S,19R,20R)-11-ethyl-2,4,
6,8,12,19-hexamethyl-7,9,14-trioxo-5-((3,4,6-
trideoxy-3-(dimethylamino)-β-D-xylo-hexopyranosyl)
oxy)-10,13-dioxa-15,18-diazatricyclo[10.6.2.0$^{15,20}$]
icos-1(18)-en-4-yl)prop-1-ynyl)-N-pyridin-3-
ylthiophene-2-carboxamide, 5-(3-((2R,4R,5R,6R,8R,11R,12S,19R,20R)-11-ethyl-2,4,
6,8,12,19-hexamethyl-7,9,14-trioxo-5-((3,4,6-
trideoxy-3-(dimethylamino)-β-D-xylo-hexopyranosyl)
oxy)-10,13-dioxa-15,18-diazatricyclo[10.6.2.0$^{15,20}$]
icos-1(18)-en-4-yl)prop-1-ynyl)-N-(4-(1,2,3-
thiadiazol-4-yl)phenyl)thiophene-2-carboxamide, 5-(3-((2R,4R,5R,6R,8R,11R,12S,19R,20R)-11-ethyl-2,4,
6,8,12,19-hexamethyl-7,9,14-trioxo-5-((3,4,6-
trideoxy-3-(dimethylamino)-β-D-xylo-hexopyranosyl)
oxy)-10, 13-dioxa-15,18-diazatricyclo[10.6.2.0$^{15,20}$]
icos-1(18)-en-4-yl)prop-1-ynyl)-N-(3-quinolin-3-
ylpropyl)thiophene-2-carboxamide, (2R,4R,5R,6R,8R,11R,12S,19R,20R)-11-ethyl-2,4,6,8,
12,19-hexamethyl-4-(3-(5-((methyl(phenylmethyl)
amino)methyl)thien-2-yl)prop-2-ynyl)-7,9,14-trioxo-
10,13-dioxa-15,18-1 diazatricyclo[10.6.2.0$^{15,20}$]icos-1
(18)-en-5-yl 3,4,6-trideoxy-3-(dimethylamino)-β-D-
xylo-hexopyranoside, or N-(5-(3-((2R,4R,5R,6R,8R,11R,12S,19R,20R)-11-ethyl-
2,4,6,8,12,19-hexamethyl-7,9,14-trioxo-5-((3,4,6-
trideoxy-3-(dimethylamino)-β-D-xylo-hexopyranosyl)
oxy)-10,13-dioxa-15,18-diazatricyclo[10.6.2.0$^{15,20}$]
icos-1(18)-en-4-yl)prop-1-ynyl)thien-2-yl)-N'-pyridin-
4-ylurea.

* * * * *